US012667383B2

(12) United States Patent
Wilson et al.

(10) Patent No.: US 12,667,383 B2
(45) Date of Patent: Jun. 30, 2026

(54) ULTRASONIC SURGICAL INSTRUMENT AND METHOD OF LATERALLY ALIGNING BLADE WITH CLAMP ARM

(71) Applicant: Cilag GmbH International, Zug (CH)

(72) Inventors: James Wilson, Cincinnati, OH (US);
Jeffrey Clark, Cincinnati, OH (US);
Andrew Conway, Cincinnati, OH (US);
Matthew Hill, Cincinnati, OH (US)

(73) Assignee: CILAG GMBH INTERNATIONAL ZUG SWITZERLAND, Zug (CH)

( * ) Notice: Subject to any disclaimer, the term of this patent is extended or adjusted under 35 U.S.C. 154(b) by 0 days.

(21) Appl. No.: 18/737,500

(22) Filed: Jun. 7, 2024

(65) Prior Publication Data

US 2025/0375214 A1 Dec. 11, 2025

(51) Int. Cl.
*A61B 17/32* (2006.01)
(52) U.S. Cl.
CPC ................. *A61B 17/320092* (2013.01); *A61B 2017/320094* (2017.08)
(58) Field of Classification Search
CPC .... A61B 17/320092; A61B 17/320068; A61B 2017/320094; A61B 2017/00115; A61B 2017/00137; A61B 2017/00181; A61B 2017/00207; A61B 2017/00367; A61B 2017/00389; A61B 2017/00407; A61B 2017/0042; A61B 2017/291; A61B 2017/320071
See application file for complete search history.

(56) References Cited

U.S. PATENT DOCUMENTS

| | | | |
|---|---|---|---|
| 5,322,055 A | 6/1994 | Davison et al. | |
| 5,873,873 A | 2/1999 | Smith et al. | |
| 5,980,510 A | 11/1999 | Tsonton et al. | |
| 6,325,811 B1 | 12/2001 | Messerly | |
| 6,773,444 B2 | 8/2004 | Messerly | |
| 6,783,524 B2 | 8/2004 | Anderson et al. | |
| 8,461,744 B2 | 6/2013 | Wiener et al. | |
| 8,479,969 B2 | 7/2013 | Shelton, IV | |

(Continued)

OTHER PUBLICATIONS

International Search Report and Written Opinion dated Aug. 22, 2025, for International Application No. PCT/IB2025/055885, 17 pages.

(Continued)

*Primary Examiner* — Anh T Dang
(74) *Attorney, Agent, or Firm* — FBT GIBBONS LLP

(57) ABSTRACT

An ultrasonic surgical instrument includes an end effector with an ultrasonic blade, a shaft assembly, and a body assembly. The shaft assembly has an articulation section, an acoustic waveguide with a flexible waveguide portion, an articulation band configured to drive articulation of the articulation section between a straight configuration and an articulated configuration, and a pin distal to the articulation section and configured to constrain a distal waveguide portion to the end effector. The body assembly has a housing, a transducer assembly, and a compensator operatively connected to the articulation band and the acoustic waveguide. The compensator is configured to longitudinally urge the acoustic waveguide to thereby pivot the ultrasonic blade about the pin for alignment relative to another portion of the end effector.

20 Claims, 18 Drawing Sheets

(56) References Cited

U.S. PATENT DOCUMENTS

| | | | |
|---|---|---|---|
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,623,027 B2 | 1/2014 | Price et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,301,759 B2 | 4/2016 | Spivey et al. | |
| 9,381,058 B2 | 7/2016 | Houser et al. | |
| 9,393,037 B2 | 7/2016 | Olson et al. | |
| 9,402,682 B2 | 8/2016 | Worrell et al. | |
| 10,034,683 B2 | 7/2018 | Monroe et al. | |
| 10,172,636 B2 | 1/2019 | Stulen et al. | |
| 11,712,228 B2 | 8/2023 | Hibner et al. | |
| 11,931,059 B2 | 3/2024 | Black et al. | |
| 11,944,341 B2 | 4/2024 | Scheib et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2012/0116265 A1 | 5/2012 | Houser et al. | |
| 2022/0125463 A1* | 4/2022 | Black | A61B 17/320092 |
| 2023/0225752 A1 | 7/2023 | Black et al. | |

OTHER PUBLICATIONS

U.S. Appl. No. 61/410,603, entitled "Energy-Based Surgical Instruments," filed Nov. 5, 2010.

* cited by examiner

ULTRASONIC SURGICAL INSTRUMENT AND METHOD OF LATERALLY ALIGNING BLADE WITH CLAMP ARM

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Such surgical instruments may be directly gripped and manipulated by a surgeon or incorporated into a robotically assisted surgery. During robotically assisted surgery, the surgeon typically operates a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller typically includes one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Such surgical instruments may be capable of articulation about an articulation joint to better access surgical sites. During this articulation, the clamp arm and blade element may move relative to one another as a portion of acoustic drivetrain within the articulation section bends resulting in relative misalignment and/or changes in tissue clamp pressure. This misalignment and/or changed tissue clamp pressure may affect treatment and increase complexity for an operator during use.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
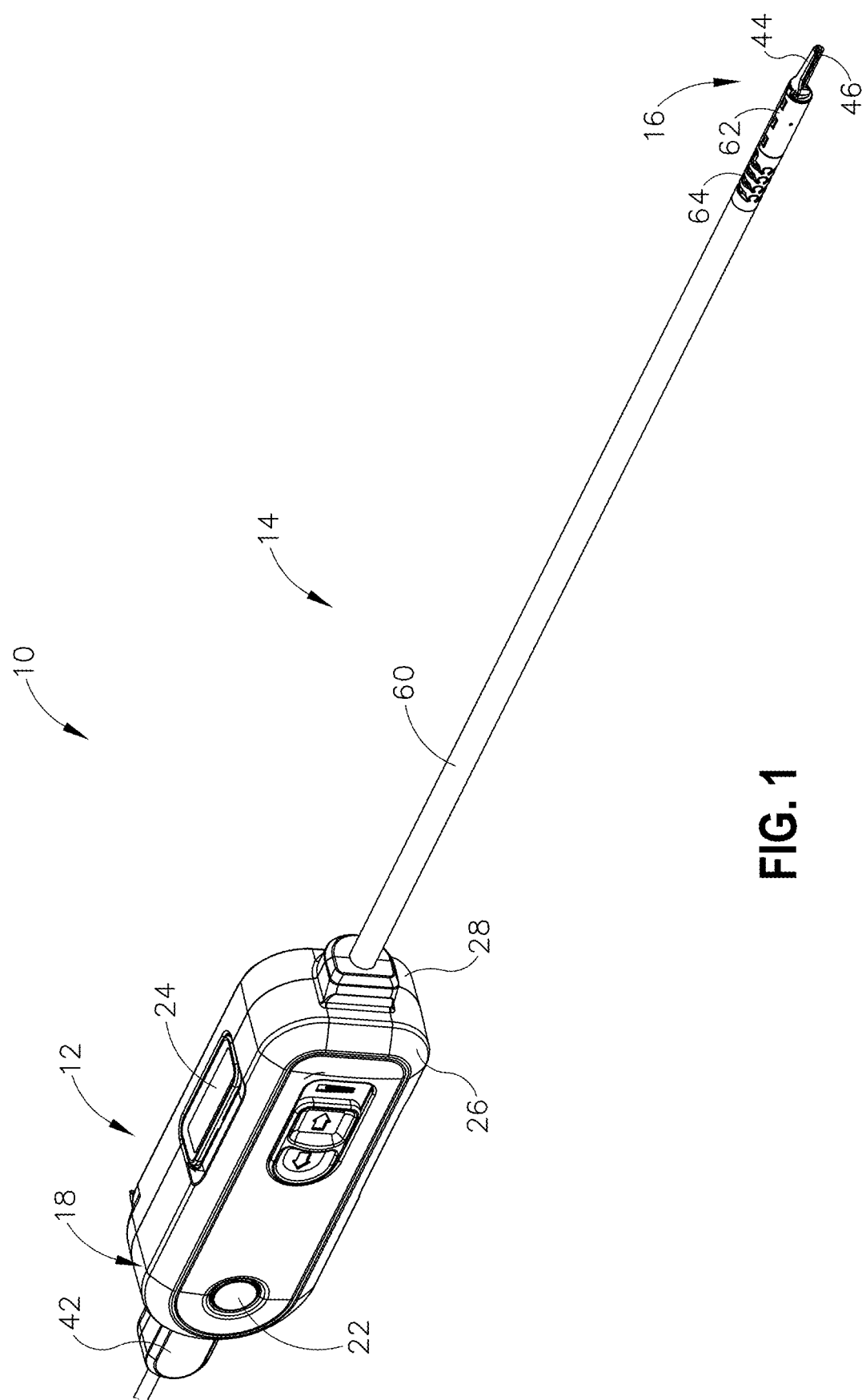
FIG. 1 depicts a front perspective view of a first example of an ultrasonic surgical instrument having an end effector, a first exemplary shaft assembly, and a first exemplary base assembly configured to connect to a robotic driven interface.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary surgical instrument, such as an ultrasonic surgical instrument (10). At least part of ultrasonic surgical instrument (10) may be constructed and operable in accordance with at least some of the teachings of any of the various patents, patent application publications, and patent applications that are cited herein. As described therein and as will be described in greater detail below, ultrasonic surgical instrument (10) is operable to cut tissue and seal or weld tissue (e.g., a blood vessel, etc.) substantially simultaneously. While the present example incorporates various ultrasonic features as ultrasonic surgical instrument (10), the invention is not intended to be unnecessarily limited to the ultrasonic features described herein.

Ultrasonic surgical instrument (10) of the present example comprises a body assembly, such as a base assembly (12), a shaft assembly (14), and an end effector (16). Base assembly (12) includes a housing (18), a button (22), and a pair of latch clasps (24). Button (22) is operatively connected to an electrical base power controller (not shown) and configured to selectively power ultrasonic surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (30) (see FIG. 5) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

Figure 2:
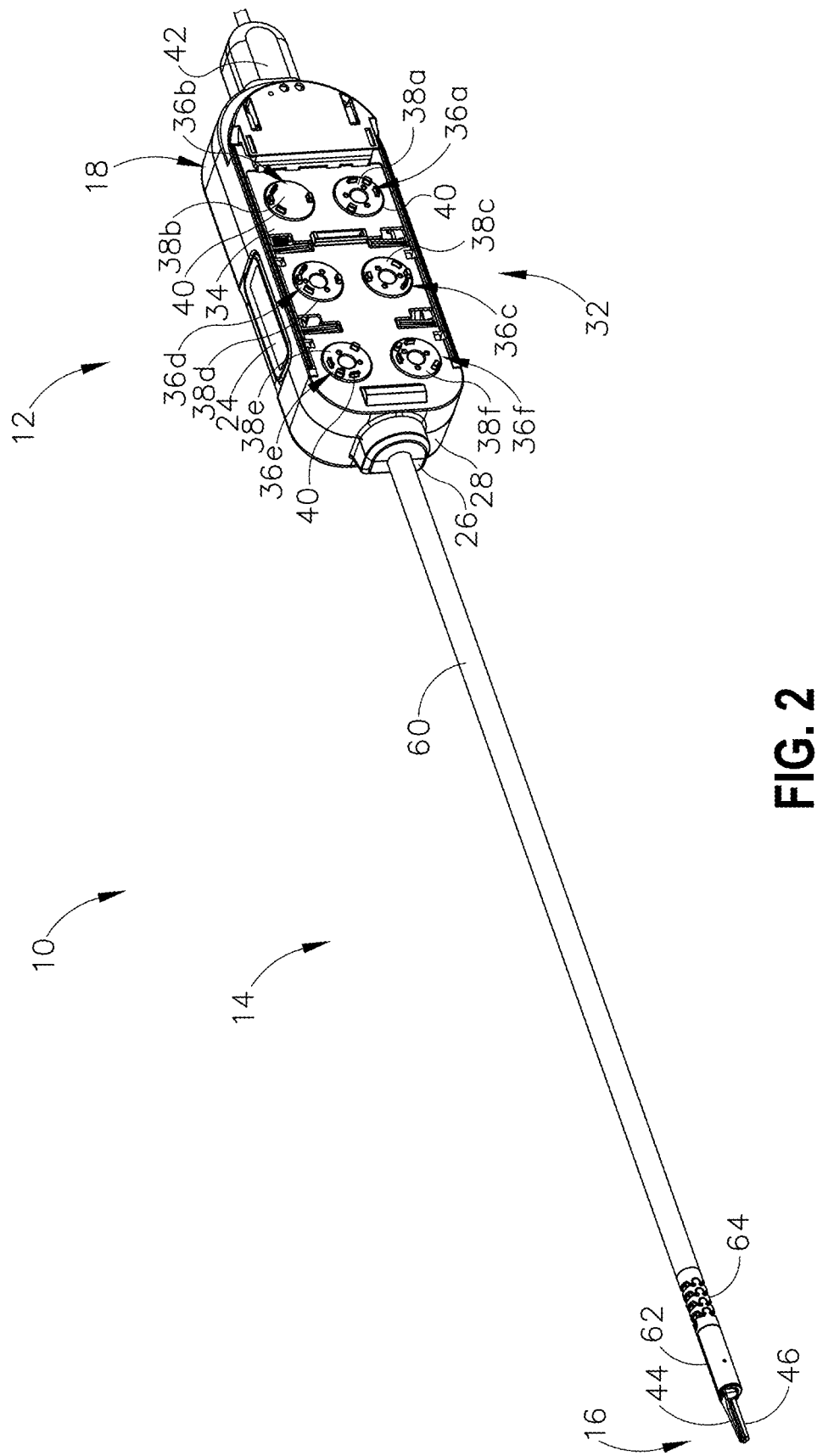
FIG. 2 depicts a rear perspective view of the ultrasonic surgical instrument of FIG. 1.

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (36a, 36b, 36c, 36d, 36e, 36f) having a plurality of input bodies (38a, 38b, 38c, 38d, 38e, 38f), respectively. Each input body (38a, 38b, 38c, 38d, 38e, 38f), which may also be referred to herein as a "puck," is configured to removably connect with the robotic drive (not shown) and, in the present example, is generally cylindrical and rotatable about an axis. Input bodies (38a, 38b, 38c, 38d, 38e, 38f) have a plurality of slots (40) configured to receive portions of the robotic drive (not shown) for gripping and rotatably driving input bodies (38a, 38b, 38c, 38d, 38e, 38f) in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16) associated with cutting, sealing, or welding tissue.

A. Exemplary End Effector and Acoustic Drivetrain

Figure 3A:
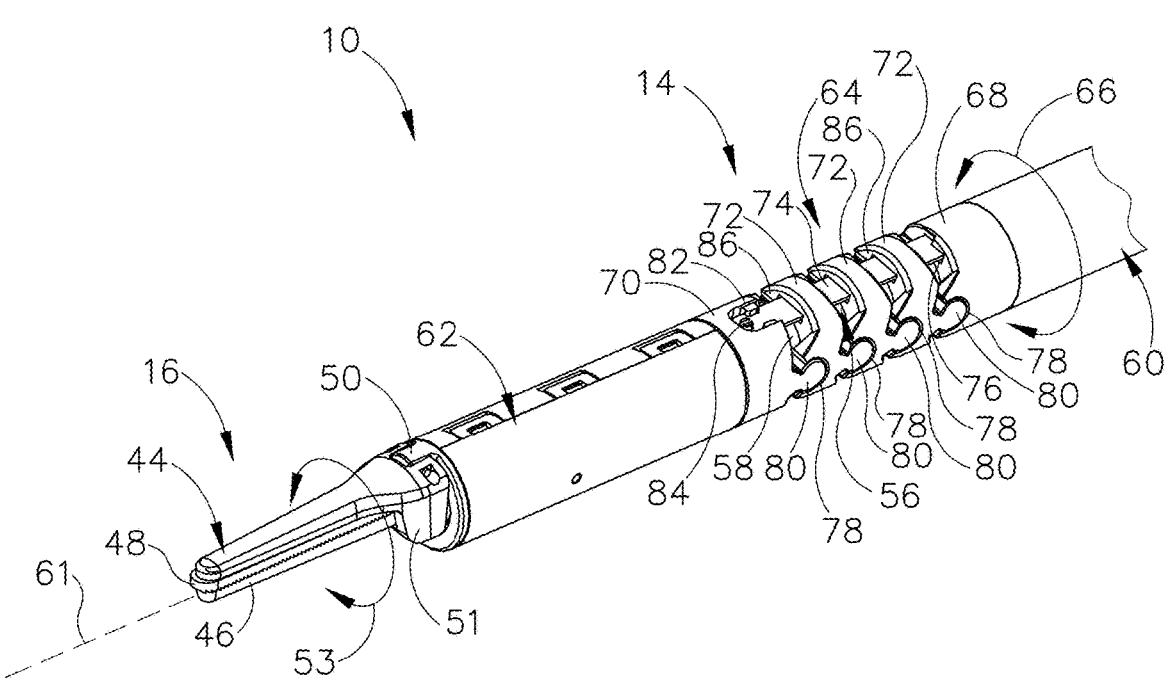
FIG. 3A depicts an enlarged perspective view of the ultrasonic surgical instrument of FIG. 1 with the end effector in a closed position and the shaft assembly in a straight configuration.
Figure 3B:
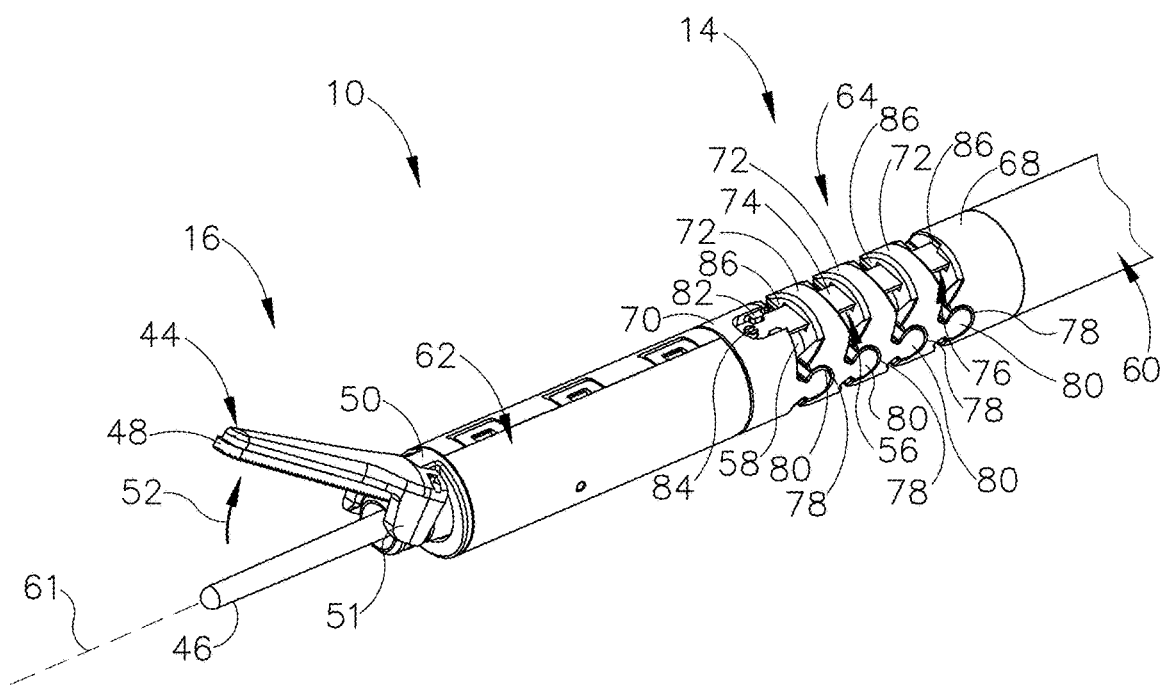
FIG. 3B depicts the enlarged perspective view of the ultrasonic surgical instrument similar to FIG. 3A, but showing the end effector in an open position.

As best seen in FIGS. 3A-3B, end effector (16) of the present example includes a clamp arm (44) and an ultrasonic blade (46). Clamp arm (44) has a clamp pad (48) secured to an underside of clamp arm (44), facing blade (46). In one example, clamp pad (48) may comprise polytetrafluoroethylene (PTFE) and/or any other suitable material(s). Clamp arm (44) is pivotally secured to a distally projecting tongue (50) of shaft assembly (14). Clamp arm (44) is operable to selectively pivot toward and away from blade (46) to selectively clamp tissue between clamp arm (44) and blade (46). A pair of arms (51) extend transversely from clamp arm (44) and are pivotally secured to another portion of shaft assembly (14) configured to longitudinally slide to pivot clamp arm (44) as indicated by an arrow (52) between a closed position shown in FIG. 3A and an open position shown in FIG. 3B.

In addition to pivoting relative to blade (46), clamp arm (44) of the present example is further configured to rotate about blade (46) relative to blade (46) and also relative to shaft assembly (14) as indicated by an arrow (53). In one example, clamp arm (44) rotates in the clockwise or counterclockwise directions completely around blade (46) and may be selectively fixed in any angular position relative to blade (46) for directing clamp arm (44) from the open position to the closed position for clamping tissue. In another example, clamp arm (44) may have rotational stops (not shown) configured to limit rotational movement of clamp arm (44) relative to blade (46) in one or more predetermined positions.

Blade (46) of the present example is operable to vibrate at ultrasonic frequencies in order to effectively cut through and seal tissue, particularly when the tissue is being compressed between clamp pad (48) and blade (46). Blade (46) is positioned at a distal end of an acoustic drivetrain. This acoustic drivetrain includes a transducer assembly (54) (see FIG. 5) and an acoustic waveguide (56), which includes a flexible portion (58) discussed below in greater detail. It should be understood that waveguide (56) may be configured to amplify mechanical vibrations transmitted through waveguide (56). Furthermore, waveguide (56) may include features operable to control the gain of the longitudinal vibrations along waveguide (56) and/or features to tune waveguide (56) to the resonant frequency of the system. Various suitable ways in which waveguide (56) may be mechanically and acoustically coupled with transducer assembly (54) (see FIG. 5) will be apparent to those of ordinary skill in the art in view of the teachings herein.

Those of ordinary skill in the art will understand that, as a matter of physics, a distal end of blade (46) is located at a position corresponding to an anti-node associated with resonant ultrasonic vibrations communicated through flexible portion (58) of waveguide (56). When transducer assembly (54) (see FIG. 5) is energized, the distal end of blade (46) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (54) (see FIG. 5) of the present example is activated, these mechanical oscillations are transmitted through waveguide (56) to reach blade (46), thereby providing oscillation of blade (46) at the resonant ultrasonic frequency. Thus, when tissue is secured between blade (46) and clamp pad (48), the ultrasonic oscillation of blade (46) may simultaneously sever the tissue and denature the proteins in adjacent tissue cells, thereby providing a coagulative effect with relatively little thermal spread. In some versions, end effector (16) is operable to apply radiofrequency (RF) electrosurgical energy to tissue in addition to applying ultrasonic energy to tissue. In any case, other suitable configurations for an acoustic transmission assembly and transducer assembly (54) will be apparent to one of ordinary skill in the art in view of the teachings herein. Similarly, other suitable configurations for end effector (16) will be apparent to those of ordinary skill in the art in view of the teachings herein.

B. Exemplary Shaft Assembly and Articulation Section

As shown in FIGS. 3A-3B, shaft assembly (14) includes a proximal shaft portion (60) extending along a longitudinal axis (61), a distal shaft portion (62) distally projecting relative to the proximal shaft portion (60), and an articulation section (64) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (64) and/or end effector (16) about longitudinal axis (61). While end effector (16) generally rotates with shaft assembly (14) as indicated by arrow (66), end effector (16) may be simultaneously and independently rotated as indicated by arrow (53) relative to shaft assembly (14) during use for repositioning portions of shaft assembly (14) and/or end effector (16) as desired.

Articulation section (64) is configured to selectively position end effector (16) at various lateral deflection angles relative to longitudinal axis (61) defined by proximal shaft portion (60). Articulation section (64) may take a variety of forms. In the present example, articulation section (64) includes a proximal link (68), a distal link (70), and a plurality of intermediate links (72) connected in series between proximal and distal links (68, 70). Articulation section (64) further includes a pair of articulation bands (74) extending along a pair of respective channels (76) collectively defined through links (68, 70, 72). Links (68, 70, 72) are generally configured to pivot relative to each other upon actuation of articulation bands (74) to thereby bend articulation section (64) with flexible portion (58) of waveguide (56) therein to achieve an articulated state. By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095, 367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034, 683, entitled "Ultrasonic Surgical Instrument with Rigidizing Articulation Drive Members," issued on Jul. 31, 2018. Alternatively, articulation section (64) may be constructed and/or operable in any other suitable fashion.

Links (68, 70, 72) shown in FIGS. 3B-4B pivotally interlock to secure distal shaft portion (62) relative to proximal shaft portion (60) while allowing for deflection of distal shaft portion (62) relative to longitudinal axis (61). In the present example, proximal link (68) is rigidly connected to proximal shaft portion (60) and has a pair of arcuate grooves (78) opposed from each other. Intermediate links (72) respectively have a pair of arcuate tongues (80) proximally extending therefrom and a pair of arcuate grooves (78) positioned distally opposite from respective tongues (80). Each intermediate link (72) has tongues (80) pivotally received within adjacent arcuate grooves (78) of another intermediate link (72) or proximal link (68) as applicable. Distal link (70) is rigidly connected to distal shaft portion (62) and has another pair of arcuate tongues (80) opposed from each other and pivotally received within adjacent arcuate grooves (78) of intermediate link (72). Tongues (80) and grooves (78) connect together to form the series of interlocked links (68, 70, 72).

Figure 4A:
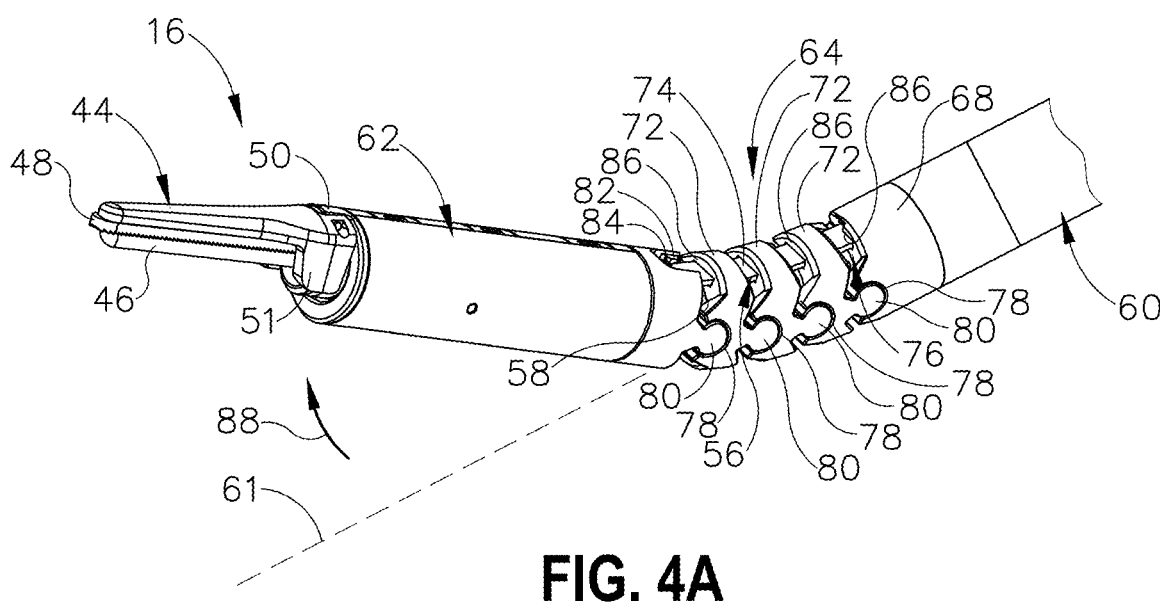
FIG. 4A depicts an enlarged perspective view of the ultrasonic surgical instrument of FIG. 1 with the end effector in a closed position and the shaft assembly in a first articulated configuration.
Figure 4B:
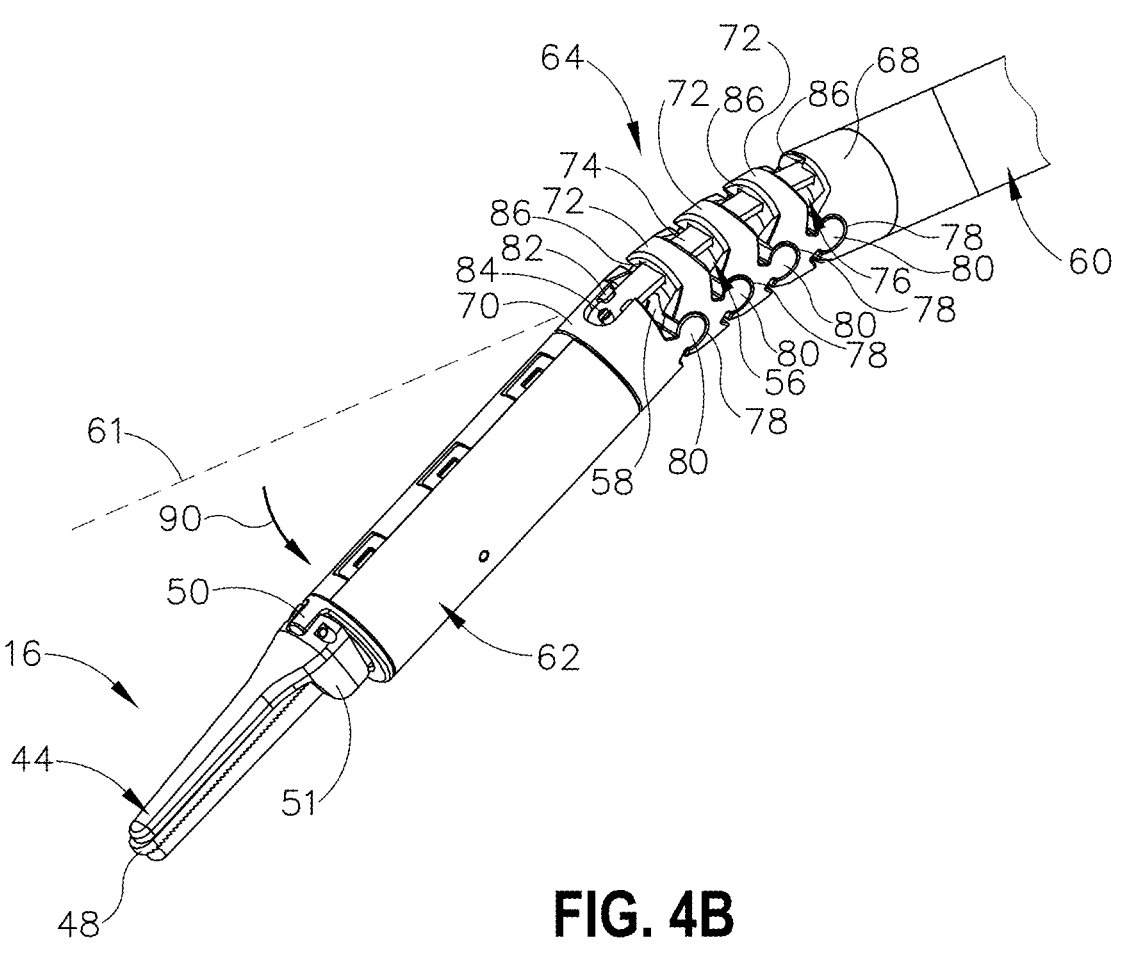
FIG. 4B depicts the enlarged perspective view of the ultrasonic surgical instrument similar to FIG. 4A, but with the shaft assembly in a second articulated configuration.

Distal link (70) further includes a pair of opposing notches (82) with a pin (84) therein configured to receive distal end portions of respective articulation bands (74). More particularly, pins (84) extend through a hole in each respective articulation bands (74) while distal end portions of respective articulation bands (74) are coupled within notches (82). Slots (86) in each of intermediate and proximal links (72, 68) longitudinally align with each other and notches (82) to collectively define channels (76) configured to receive articulation bands (74) while allowing articulation bands (74) to slide relative to links (68, 70, 72). To this end, when articulation bands (74) translate longitudinally in an opposing fashion, this will cause articulation section (64) to bend, thereby laterally deflecting end effector (16) away from the longitudinal axis (61) of proximal shaft portion (60) from a straight configuration as shown in FIG. 3B to a first articulated configuration as shown in FIG. 4A and indicated by an arrow (88) or a second articulated configuration as shown in FIG. 4B and indicated by an arrow (90). In particular, end effector (16) will be articulated toward the articulation band (74) that is being pulled proximally. During such articulation, the other articulation band (74) may be pulled distally. Alternatively, the other articulation band (74) may be driven distally by an articulation control. Furthermore, flexible acoustic waveguide (56) is configured to effectively communicate ultrasonic vibrations from waveguide (56) to blade (46) even when articulation section (64) is in an articulated configuration as shown in FIGS. 4A-4B.

C. Exemplary Base Assembly with Instrument Actuators for Robotic Interface

Figure 5:
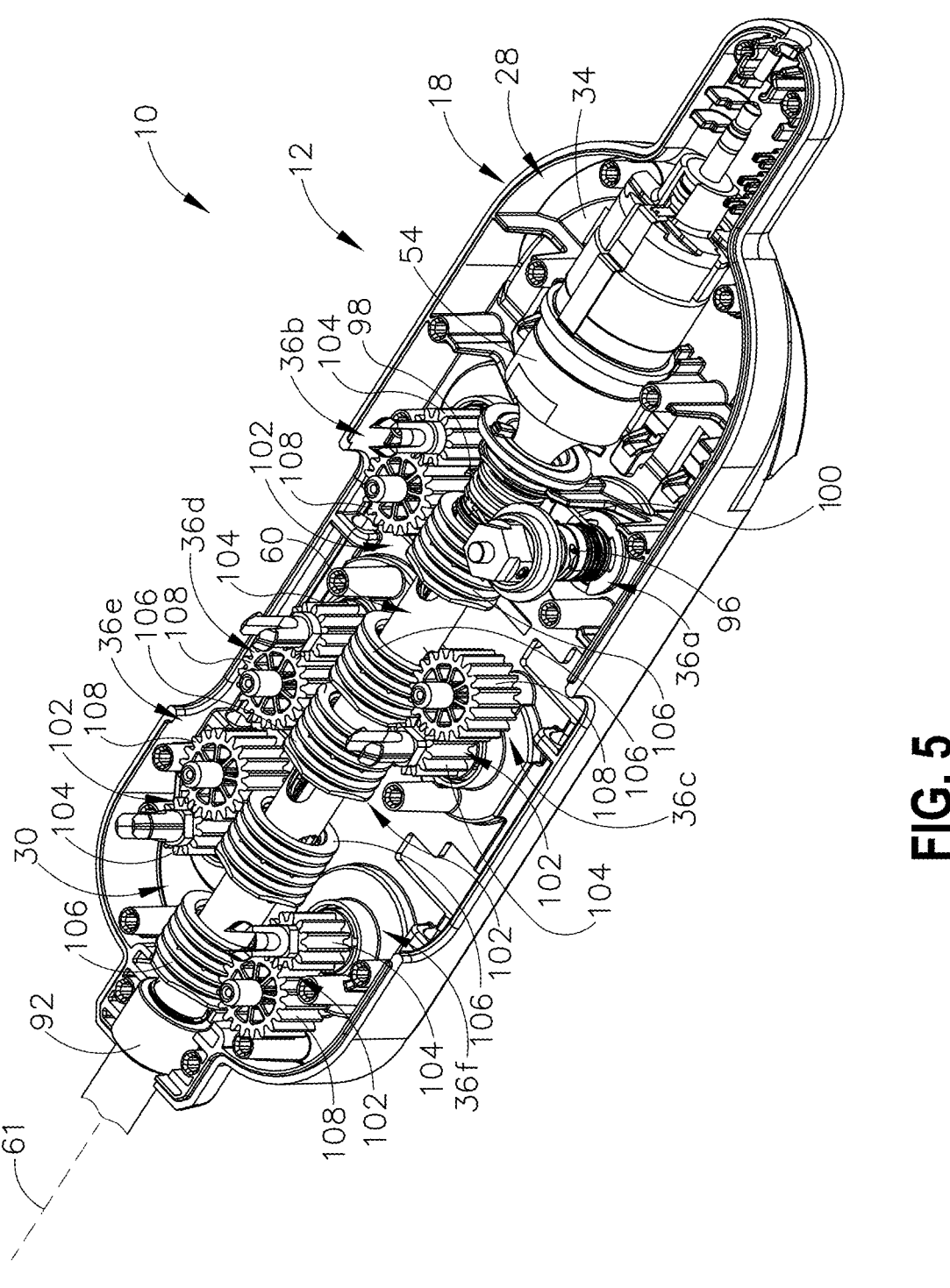
FIG. 5 depicts an enlarged perspective view of the ultrasonic surgical instrument of FIG. 1 with the base assembly having various components removed for greater clarity of an interior space of the base assembly.

FIG. 5 shows interior space (30) of base assembly (12) with instrument actuators (36a, 36b, 36c, 36d, 36e, 36f) in greater detail. Generally, instrument actuators (36a, 36b, 36c, 36d, 36e, 36f) are engaged with shaft assembly (14) and configured to direct movement of end effector (16) and/or shaft assembly (14), such as movement indicated above in one example by arrows (52, 53, 66, 88, 90) (see FIGS. 3A-4B). Shaft assembly (14) is received within base assembly (12) and supported by bearings (92) therein to operatively connect each respective instrument actuator (36a, 36b, 36c, 36d, 36e, 36f) to shaft assembly (14) as well as operatively connect acoustic waveguide (56) (see FIG. 3A) to transducer assembly (54) and a generator (not shown) of the acoustic drivetrain. More particularly, transducer assembly (54) is coupled with generator (not shown) such that transducer assembly (54) receives electrical power from generator (not shown). Piezoelectric elements (not shown) in transducer assembly (54) convert that electrical power into ultrasonic vibrations. Generator (not shown) may be coupled to the electrical power source (not shown) via electrical plug (42) (see FIG. 1) and a control module (not shown) that are configured to provide a power profile to transducer assembly (54) that is particularly suited for the generation of ultrasonic vibrations through transducer assembly (54). By way of example only, generator (not shown) may comprise a GEN04 or GEN11 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Still other suitable forms that generator (not shown) may take, as well as various features and operabilities that generator (not shown) may provide, will be apparent to those of ordinary skill in the art in view of the teachings herein.

Figure 6:
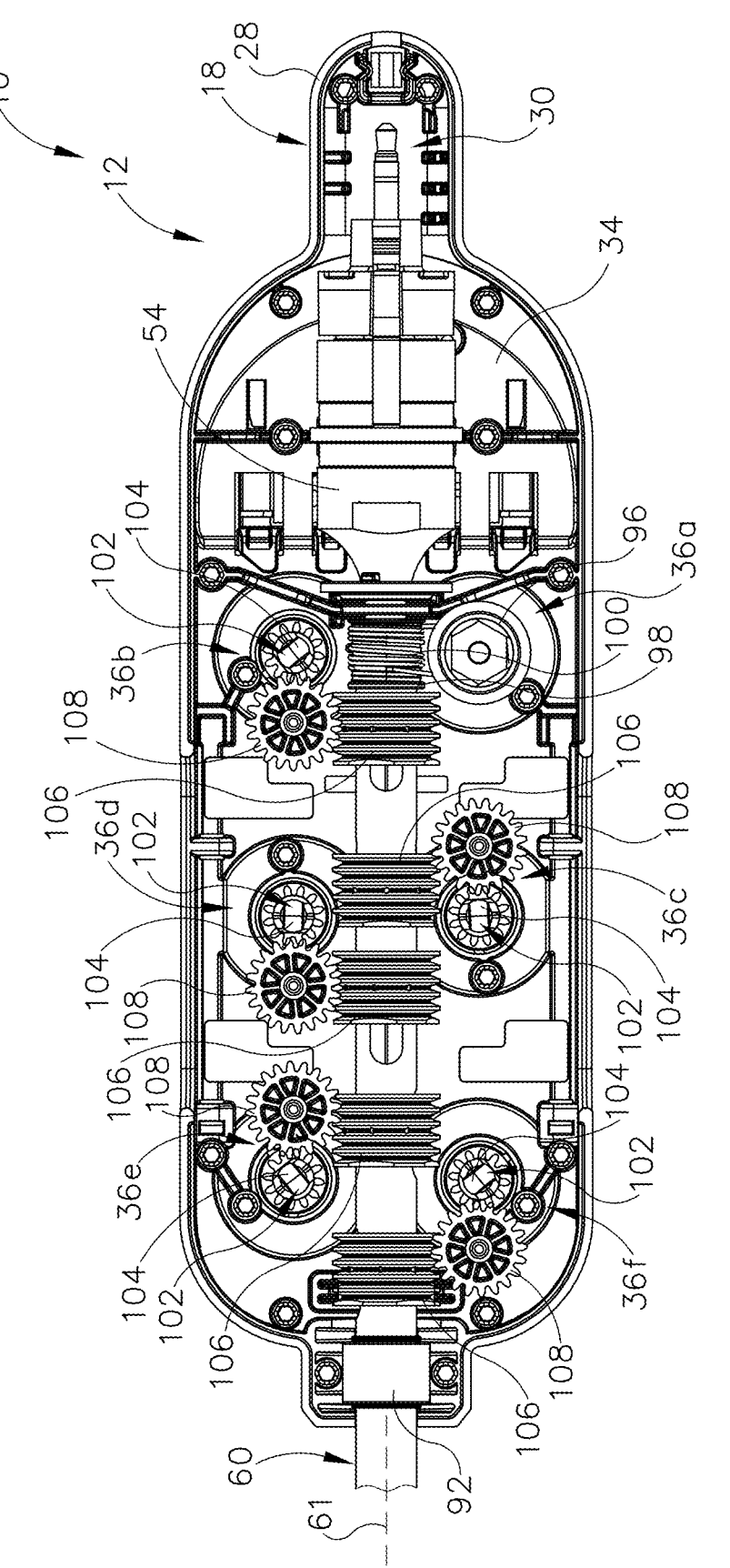
FIG. 6 depicts an enlarged front view of the ultrasonic surgical instrument of FIG. 1 with the base assembly having various components removed for greater clarity of the interior space of the base assembly.

The present example of base assembly (12) shown in FIGS. 5-6 includes six instrument actuators (36a, 36b, 36c, 36d, 36e, 36f), although it will be appreciated that any such number of such instrument actuators (36a, 36b, 36c, 36d, 36e, 36f) configured to direct movement of shaft assembly (14) and/or end effector (16) may be similarly used. As shown with respect to operation of ultrasonic surgical instrument (10), instrument actuator (36a) is more particularly a roll system actuator (36a) configured to rotate shaft assembly (14) about longitudinal axis (61). In contrast, instrument actuators (36b, 36c, 36d, 36e, 36f) are linear system actuators (36b, 36c, 36d, 36e, 36f) configured to translationally drive movement of portions of end effector (16) and/or shaft assembly (14) while simultaneously allowing for rotation of shaft assembly (14) via roll system actuator (36a).

Roll system actuator (36a) in one example includes a drive spool (96) rigidly connected to puck (38a) (see FIG. 2) and a driven spool (98) rigidly connected to proximal shaft portion (60) within housing (18). Drive spool (96) is mounted to rotate with puck (38*a*) (see FIG. 2) about a common puck axis, whereas driven spool (98) is mounted to rotate with proximal shaft portion (60) about the longitudinal axis (61). A cable (100) wraps around each of the drive and driven spools (96, 98), accommodating the differing orientation of the puck axis and longitudinal axis (61), such that rotating drive spool (96) via puck (38*a*) (see FIG. 2) urges rotation of driven spool (98). In turn, shaft assembly (14), including proximal and distal shaft portions (60, 62) rotates about longitudinal axis (61) as indicated by arrow (66) (see FIG. 3A), such as by robotically driven actuation of puck (38*a*) (see FIG. 2).

Linear system actuators (36*b*, 36*c*, 36*d*, 36*e*, 36*f*) of the present example include a gear-rack mechanism (102) having a rotatable drive gear (104), a translatable rack gear (106), and an idler gear (108) connected therebetween. Drive gears (104) are respectively connected to and rigidly project from pucks (38*b*, 38*c*, 38*d*, 38*e*, 38*f*) (see FIG. 2), whereas each rack gear (106) is connected to another portion of proximal shaft portion (60) directing movement of shaft assembly (14) and/or end effector (16) as discussed above. Each rack gear (106) is cylindrical and rigidly connected relative to proximal shaft portion (60) to rotate therewith. Rack gear (106) is thereby configured to rotate with shaft assembly (14) while remaining meshed with idler gear (108). Rotating respective pucks (38*b*, 38*c*, 38*d*, 38*e*, 38*f*) (see FIG. 2) thus respectively rotates drive gears (104) and idler gears (108) to translate rack gears (106) as desired.

In the present example, with respect to FIGS. 2-4B and FIG. 6, linear system actuator (36*b*) has puck (38*b*) operatively connected to clamp arm (44) to direct movement of clamp arm (44) between the open and closed positions according to arrow (52). Linear system actuators (36*c*, 36*d*) have respective pucks (38*c*, 38*d*) operatively connected to clamp arm (44) to direct movement of clamp arm (44) around blade (46) in both the clockwise and counterclockwise directions according to arrow (53). In addition, linear system actuators (36*e*, 36*f*) have respective pucks (38*e*, 38*f*) operatively connected to articulation bands (74) to direct movement of articulation section (64) according to arrows (88, 90) for deflecting end effector (16) relative to longitudinal axis (61). Of course, in other examples, instrument actuators (36*a*, 36*b*, 36*c*, 36*d*, 36*e*, 36*f*) may be alternatively configured with more or less actuators (36*a*, 36*b*, 36*c*, 36*d*, 36*e*, 36*f*) and/or more or less movement as desired. The invention is thus not intended to be unnecessarily limited to instrument actuators (36*a*, 36*b*, 36*c*, 36*d*, 36*e*, 36*f*) or particular movements of shaft assembly (14) and/or end effector (16) as described in the present example.

II. Exemplary Shift of Acoustic Drivetrain with Shaft Assembly Articulation

Figure 7A:
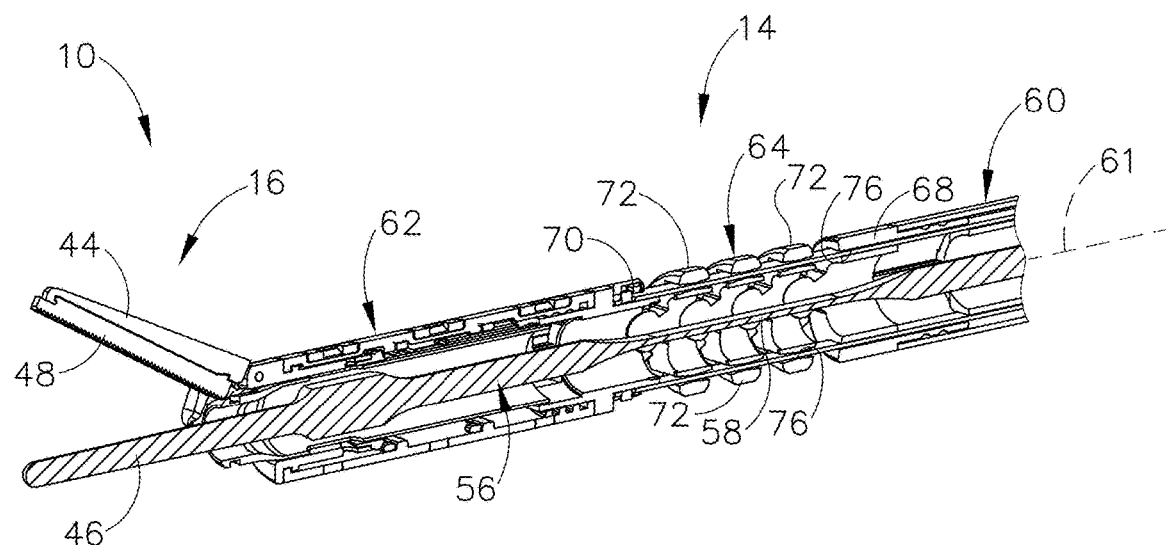
FIG. 7A depicts an enlarged, sectional, perspective view of the ultrasonic surgical instrument of FIG. 1 taken along a centerline thereof showing an ultrasonic blade of the end effector positioned relative to a clamp arm of the end effector with the shaft assembly in the straight configuration.
Figure 7B:
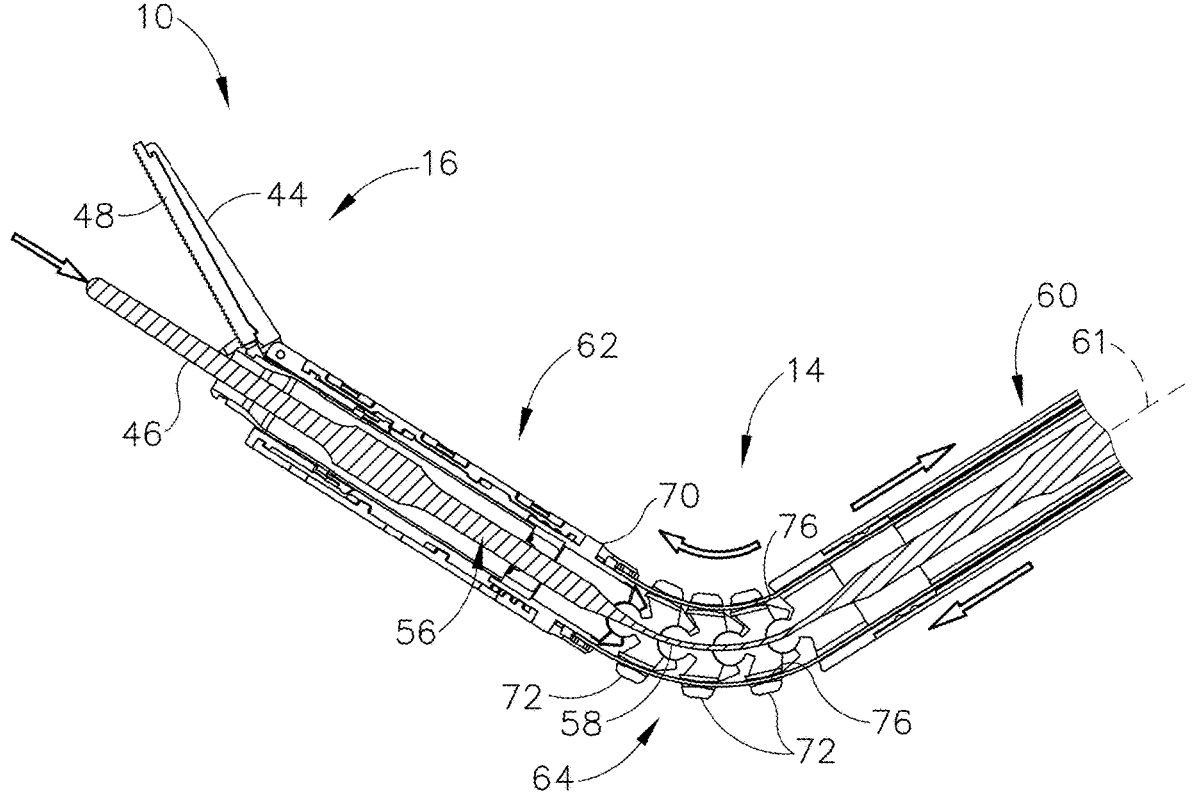
FIG. 7B depicts an enlarged, cross-sectional view of the ultrasonic surgical instrument of FIG. 7A taken along a centerline thereof showing the ultrasonic blade of the end effector positioned relative to the clamp arm of the end effector with the shaft assembly in the first articulated configuration.
Figure 8A:
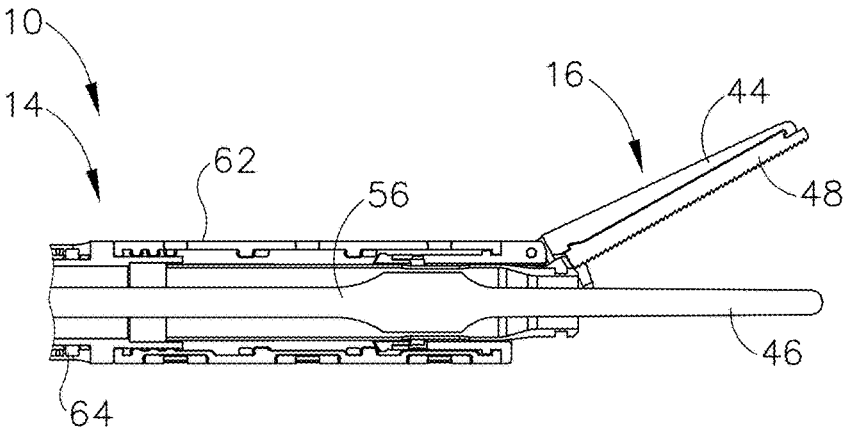
FIG. 8A depicts an enlarged, cross-sectional view of the end effector and the shaft assembly taken along a centerline thereof showing the ultrasonic blade positioned relative to the clamp arm with the shaft assembly in the straight configuration.
Figure 8B:
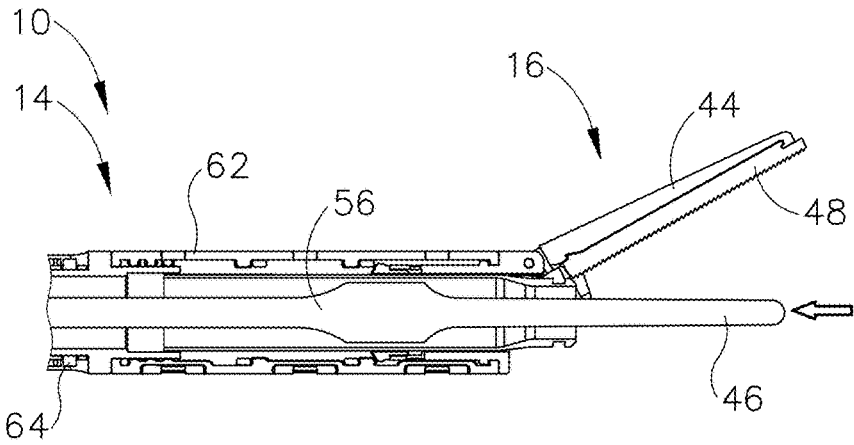
FIG. 8B depicts the enlarged, cross-sectional view of the end effector and the shaft assembly similar to FIG. 8A, but showing the ultrasonic blade positioned relative to the clamp arm with the shaft assembly in the first articulated configuration.

With respect to FIGS. 7A-8B, in one example, the distal tip of blade (46) is positioned to align in a predetermined alignment with a distal tip of clamp arm (44) in the straight configuration as shown in FIG. 7A and FIG. 8A. More particularly, such predetermined alignment positions the distal tip of blade (46) longitudinally flush with distal tip of clamp arm (44) in the closed position so that the distal tips of blade (46) and clamp arm (44) are positioned in a common plane perpendicular to an axis defined by blade (46). As articulation section (64) articulates from the straight configuration toward the articulated configuration as shown in FIG. 7B and FIG. 8B, articulation section (64) essentially elongates as the radius of curvature along articulation section (64) increases. In turn, blade (46) moves proximally relative to clamp arm (44) such that the distal tip of blade (46) and the distal tip of clamp arm (44) are no longer longitudinally aligned in the predetermined alignment due to a constant longitudinal length of acoustic waveguide (56) and blade (46) from transducer assembly (54) (see FIG. 6) to the distal tip of blade (46).

In some instances, it may be desirable to longitudinally adjust blade (46) relative to clamp arm (44) so as to maintain the predetermined alignment between blade (46) and clamp arm (44) with articulation section (64) in the straight and articulated configurations. Given the constant longitudinal length of acoustic waveguide (56) and blade (46), a proximal portion of the acoustic drivetrain, such as transducer assembly (54) (see FIG. 5), may be shifted in order to offset shift at a distal portion of the acoustic drivetrain, such as blade (46). To this end, a shiftable transducer assembly (254, 354) (see FIGS. 10A-11B) may be incorporated into ultrasonic surgical instrument (10) to align blade (46) with clamp arm (44) as desired, such as shown in FIG. 8A. In an alternative example shown in FIG. 9, an ultrasonic surgical instrument (210) has a pin (109) extending through a node of acoustic waveguide (56) and distal shaft portion (62) to fix acoustic waveguide (56) relative to distal shaft portion (62). In turn, pin (110) also longitudinally secures blade (46) in the predetermined alignment position relative to clamp arm (44). Still, the invention is not intended to be unnecessarily limited to mechanically fixing blade (46) relative to clamp arm (44). Moreover, such longitudinal adjustments of one or more portions of the acoustic drivetrain along longitudinal axis (61) (see FIG. 7B) may be performed in an alternative ultrasonic surgical instrument (not shown) without a clamp arm (not shown) or even to achieve other alignments relative to the acoustic drivetrain without regard for articulation of articulation section (64). The invention is thus not intended to be unnecessarily limited to use for maintaining the predetermined alignment between clamp arm (44) and blade (46) as shown and described herein. In any case, like numbers below indicate like features described above in greater detail.

A. Passively Shiftable Transducer Assembly

Figure 9:
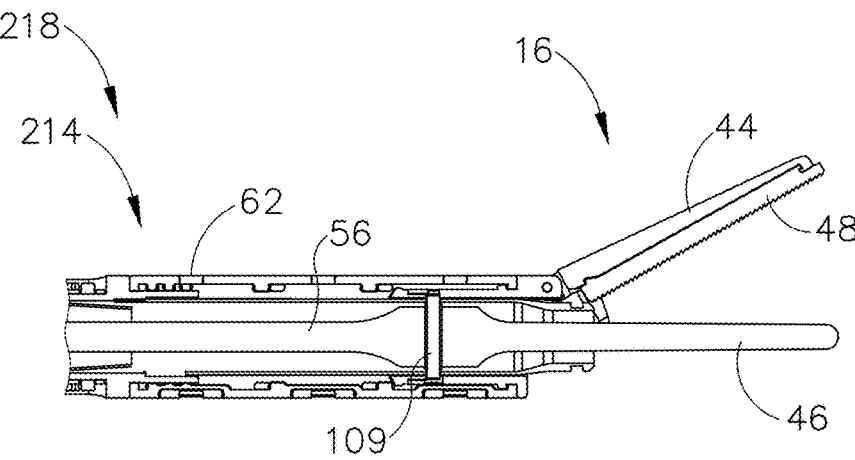
FIG. 9 depicts an enlarged, cross-sectional view of a second example of an ultrasonic surgical instrument taken along a centerline thereof with the end effector of FIG. 1 and a second exemplary shaft assembly having the ultrasonic blade fixed relative to the clamp arm in the straight configuration and the articulated configuration.
Figure 10A:
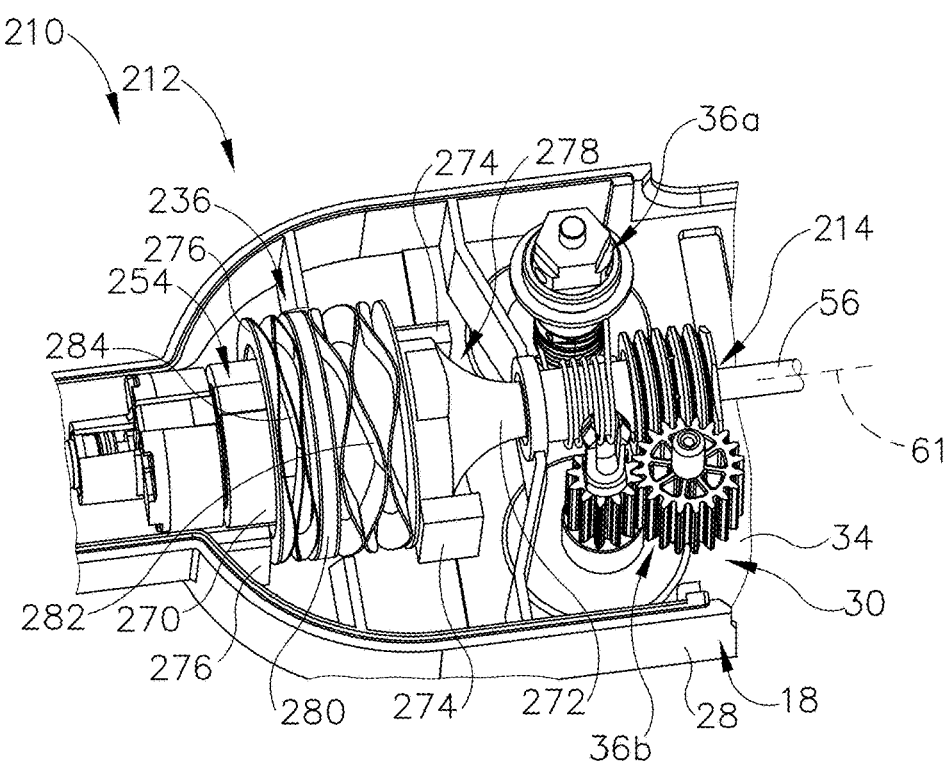
FIG. 10A depicts an enlarged, perspective view of a second exemplary base assembly of the ultrasonic surgical instrument of FIG. 9 having various components removed for greater clarity of a passively shiftable transducer assembly in a proximal position while the shaft assembly of FIG. 9 is in the straight configuration.
Figure 10B:
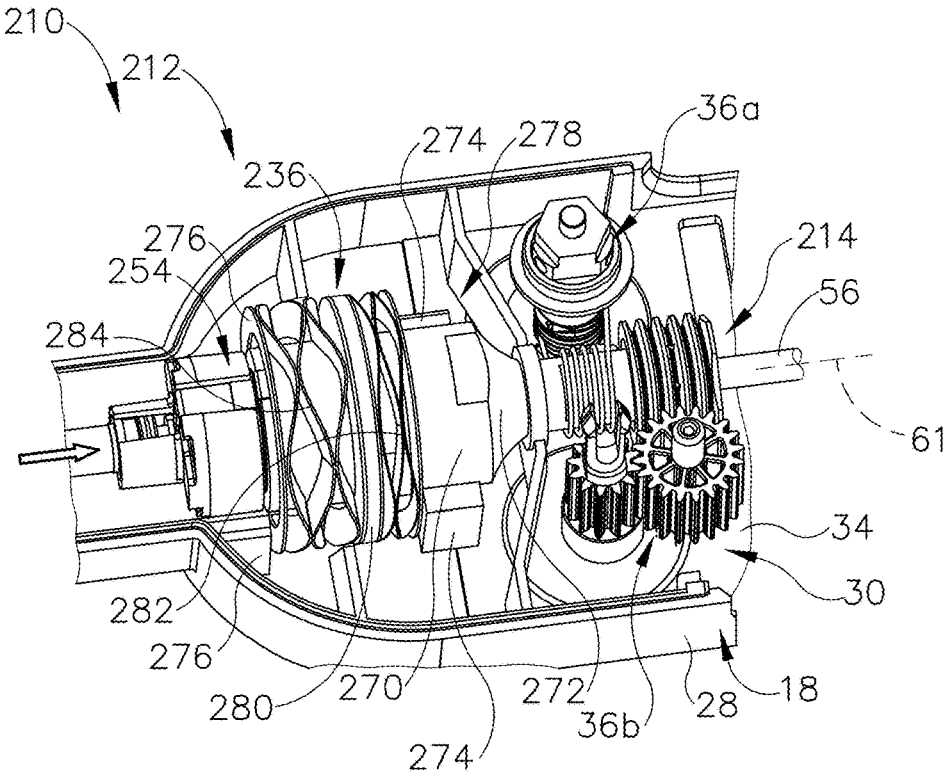
FIG. 10B depicts the enlarged, perspective view of the base assembly similar to FIG. 10A, but showing the passively shiftable transducer assembly in a distal position while the shaft assembly of FIG. 9 is in the articulated configuration.

FIGS. 9-10B show a second example of an ultrasonic surgical instrument (210) having end effector (16) and a second exemplary shaft assembly (214) with pin (109) through acoustic waveguide (56) such that blade (46) is longitudinally fixed in the predetermined alignment with clamp arm (44) as discussed above in greater detail. Ultrasonic surgical instrument (210) further includes a second exemplary base assembly (212) constructed similarly to base assembly (12) (see FIG. 6), but with a passively shiftable transducer assembly (254) and a passive system actuator (236). Shiftable transducer assembly (254) is movably coupled between housing (18) and passive system actuator (236) such that passive system actuator (236) enables shiftable transducer assembly (254) to be urged proximally or distally along longitudinal axis (61). Thereby, shiftable transducer assembly (254) accommodates longitudinal movement of acoustic waveguide (56) and blade (46) for maintaining the predetermined alignment. In the present example, pin (109) distally pulls on acoustic waveguide (56) when deflecting end effector away from longitudinal axis (61) such that shiftable transducer assembly (254) distally pulls shiftable transducer assembly (254) toward end effector (16) and along longitudinal axis (61). In contrast, pin (109) proximally pushes on acoustic waveguide (56) when deflecting end effector toward longitudinal axis (61) such that shiftable transducer assembly (254) proximally pushes shiftable transducer assembly (254) away from end effector (16) and along longitudinal axis (61). Shiftable transducer assembly (254) and system actuator (236) are thus referred to herein as "passive" given that shiftable transducer assembly (254) and system actuator (236) enable movement rather than providing initiating force for such movement. Although, as will be described below in greater detail, shiftable transducer assembly (254) and system actuator (236) may still provide force, such as a reactionary force, for maintaining tension and/or compression on acoustic waveguide (56).

Shiftable transducer assembly (254) of the present example shown in FIGS. 10A-10B more particularly includes a transducer housing (270) and a transducer horn (272) threaded into engagement with acoustic waveguide (56). Housing (18), in one example, has a pair of distal mount seats (274) and a pair of proximal mount seats (276) configured to longitudinally capture passive system actuator (236) while simultaneously allowing for longitudinal movement of transducer housing (270) and transducer horn (272) through a central space (278). Passive system actuator (236) thereby resiliently and translatably supports shiftable transducer assembly (254) relative to housing (18) along longitudinal axis (61), although it will be appreciated that the invention is not intended to be unnecessarily limited to resilient or translational mounting within housing (18).

More particularly, passive system actuator (236) of the present example includes an annular base seat (280) rigidly connected to and extending radially outward from transducer housing (270) as well as a distal annular spring (282) and a proximal annular spring (284). Distal annular spring (282) seats in compression between annular base seat (280) and distal mount seats (274) while proximal annular spring (284) seats in compression between annular base seat (280) and proximal mount seats (276). Distal and proximal mounts seats (274, 276) also laterally secure annular base seat (280) with transducer housing (270) on longitudinal axis (61). With respect to FIG. 10A, shiftable transducer assembly (254) is in a proximal position on longitudinal axis (61) while articulation section (64) (see FIG. 7A) is in a straight configuration (see FIG. 7A). In contrast, with respect to FIG. 10B, shiftable transducer assembly (254) is in a distal position on longitudinal axis (61) while articulation section (64) (see FIG. 7B) is in an articulated configuration (see FIG. 7B). In any longitudinal position between the distal and proximal positions, distal and proximal annular springs (282, 284) effectively balance force applied by pin (109) (see FIG. 9) while annular base seat (280) translatably supports transducer housing (270) relative to housing (18) of base assembly (212). As shown in the present example, distal and proximal annular springs (282, 284) are in compression. More particularly, compression of distal annular spring (282) increases while compression of proximal annular spring (284) decreases as shiftable transducer assembly (254) moves from the proximal position toward the distal position. Also, compression of distal annular spring (282) decreases while compression of proximal annular spring (284) increases as shiftable transducer assembly (254) moves from the distal position toward the proximal position.

Distal and proximal annular springs (282, 284) are configured to balance annular base seat (280) with transducer housing (270) supported therein according to a predetermined balance in any longitudinal position for accommodating movement of acoustic waveguide (56) resulting from articulation of articulation section (64) (see FIG. 7A). In one example, distal and proximal annular springs (282, 284) balance acoustic waveguide (56) in tension between the proximal and distal positions. In another example, distal and proximal annular springs (282, 284) balance acoustic waveguide (56) in compression between the proximal and distal positions. In still another example, distal and proximal annular springs (282, 284) balance acoustic waveguide (56) in compression toward the proximal position and in tension toward the distal position with a neutral, non-compression and non-tension state therebetween. In still yet another example, distal and proximal annular springs (282, 284) balance acoustic waveguide (56) in tension toward the proximal position and in compression toward the distal position with another neutral, non-compression and non-tension state therebetween. The invention is thus not intended to be unnecessarily limited to maintaining one or more portions of the acoustic drivetrain, such acoustic waveguide (56), in a particular state of compression or tension.

In use, with respect to FIGS. 6 and 9-10B, linear system actuators (36e, 36f) urge articulation bands (74) (see FIG. 7B) to direct movement of articulation section (64) for deflecting end effector (16) relative to longitudinal axis (61). Articulation section (64) articulates from the straight configuration toward the articulated configuration such that pin (84) distally pulls acoustic waveguide (56) with shiftable transducer assembly (254) from the proximal position toward the distal position to maintain the predetermined alignment between blade (46) and clamp arm (44). In this respect, movement of shiftable transducer assembly (254) is dependent upon articulation of articulation section (64). Annular base seat (280) of passive system actuator (236) supports transducer housing (270) and transducer horn (272) as shiftable transducer assembly (254) translates from the proximal position toward the distal position. In addition, annular base seat (280) compresses distal annular spring (282) against distal mount seats (274), while proximal annular spring (284) expands, distally urging annular base seat (280) toward distal mount seats (274). Distal and proximal annular springs (282, 284) continue to balance shiftable transducer assembly (254) and acoustic waveguide (56) with pin (109) as articulation section (64) is positioned in the articulated configuration during use. Thus, blade (46) remains in the same predetermined alignment with clamp arm (44) before, during, and after articulation of articulation section (64). Of course, any alignment may be desired, and the invention is not intended to be limited to the alignment of blade (46) shown and described in the present example. While the present example describes movement of articulation section (64) from the straight configuration toward the articulated configuration, it will be appreciated that shiftable transducer assembly (254) and associated components will move in opposite directions from those discussed above when moving articulation section (64) from the articulated configuration toward the straight configuration. Furthermore, in another example, articulation of articulation section (64) may be controlled by an operator via a handle assembly (not shown), such as by a knob (not shown) operatively connected to articulation section (64), rather than a robotic drive (not shown). The invention is thus not intended to be unnecessarily limited to use with base assembly (212) as shown and described herein.

B. Actively Shiftable Transducer Assembly

Figure 11A:
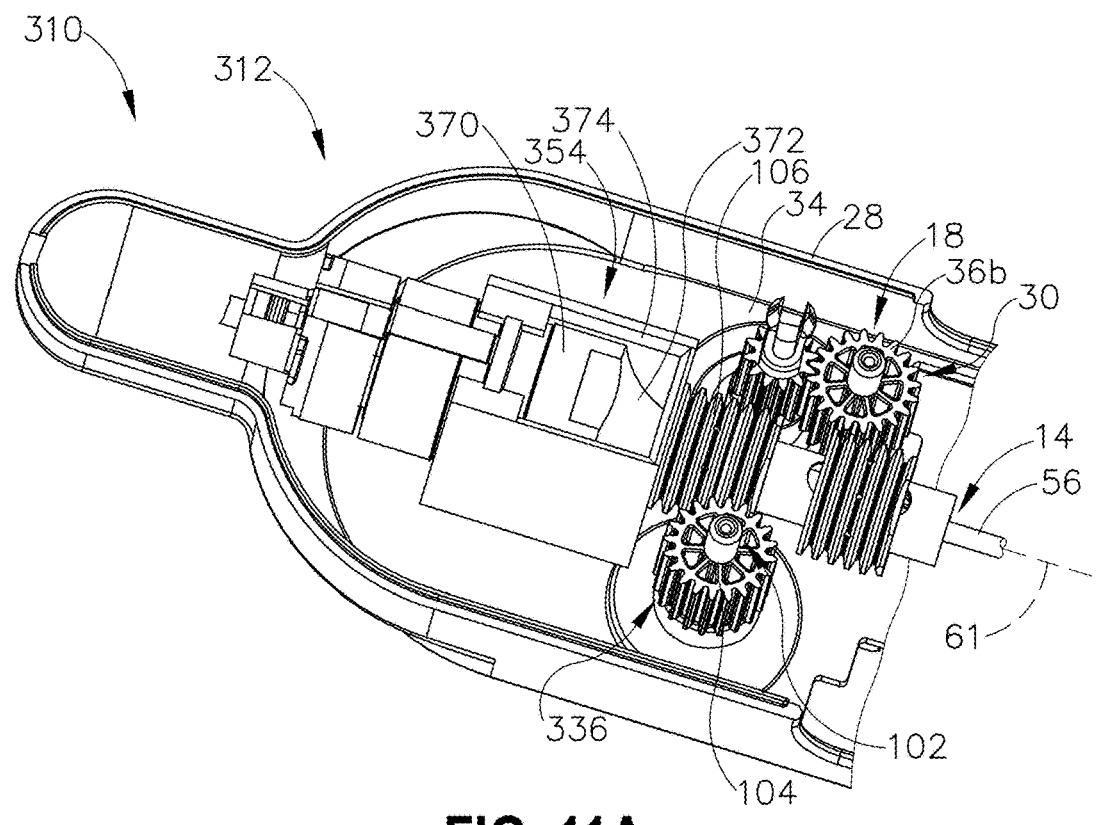
FIG. 11A depicts an enlarged perspective view of a third example of an ultrasonic surgical instrument with a third exemplary base assembly having various components removed for greater clarity of an actively shiftable transducer assembly in a proximal position.
Figure 11B:
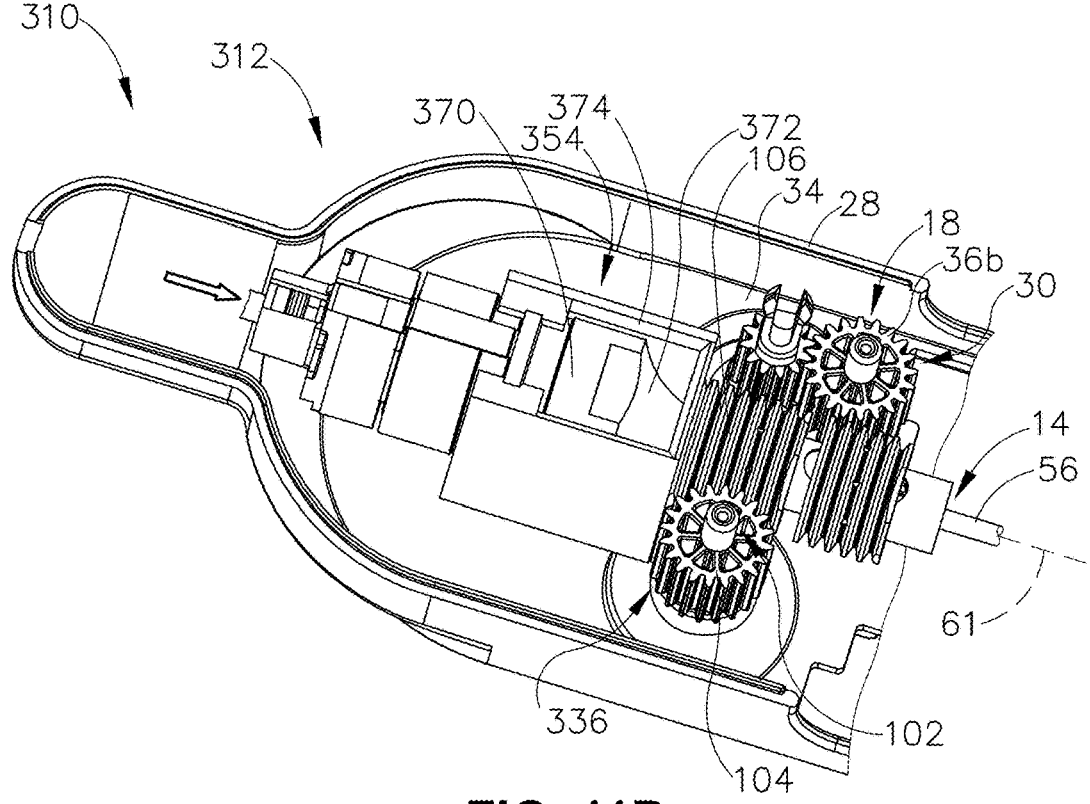
FIG. 11B depicts the enlarged, perspective view of the base assembly similar to FIG. 11A, but showing the actively shiftable transducer assembly in a distal position.

FIGS. 11A-11B show a third example of an ultrasonic surgical instrument (310) having end effector (16) (see FIG. 8A) and shaft assembly (14) without pin (109) (see FIG. 9) through acoustic waveguide (56) such that blade (46) may or may not be longitudinally maintained in the predetermined alignment with clamp arm (44). Ultrasonic surgical instrument (310) further includes a third exemplary base assembly (312) constructed similarly to base assembly (12) (see FIG. 6), but with an actively shiftable transducer assembly (354) and an active system actuator (336). Shiftable transducer assembly (354) is movably coupled between housing (18) and active system actuator (336) such that active system actuator (336) urges shiftable transducer assembly (354) proximally or distally along longitudinal axis (61). In one example, active system actuator (336) keys movement of shiftable transducer assembly (354) to accommodate longitudinal movement of acoustic waveguide (56) and blade (46) (see FIG. 8A) for maintaining the predetermined alignment during articulation. Either shaft assembly (14) or shaft assembly (214) (see FIG. 9) may be incorporated into ultrasonic surgical instrument (310) in such an example. In another example, active system actuator (336) directs movement of shiftable transducer assembly (354) to position blade (46) in any longitudinal position relative to shaft assembly (14) and/or clamp arm (44) as desired by the operator. The invention is thus not intended to be unnecessarily limited to acoustic waveguide (56) being movable or fixed, such as via pin (109). Shiftable transducer assembly (354) and system actuator (336) are thus referred to herein as "active" given that shiftable transducer assembly (354) and system actuator (336) initiate movement by force rather than simply supporting such movement.

Shiftable transducer assembly (354) of the present example shown in FIGS. 11A-11B more particularly includes a transducer housing (370) and a transducer horn (372) threaded into engagement with acoustic waveguide (56). Active system actuator (336) of the present example includes gear-rack mechanism (102) with rotatable drive gear (104) and translatable rack gear (106) discussed above in greater detail as well as a transducer coupler (374) rigidly extending in the proximal direction from rack gear (106). Transducer coupler (374) receives transducer housing (370) to longitudinally secure transducer housing (370) and transducer horn (372) relative to rack gear (106) distally extending therefrom while laterally supporting transducer housing (370) and transducer horn (372). Rotatable drive gear (104) directly engages with rack gear (106) in the present example to selectively translate shiftable transducer assembly (354) as desired.

In use, with respect to FIGS. 8A and 11A-11B, drive gear (104) is selectively rotated via robotic drive (not shown) to linearly translate rack gear (106) along longitudinal axis (61) as desired. In turn, transducer coupler (374) urges shiftable transducer assembly (354) distally or proximally along longitudinal axis (61) thereby translating acoustic waveguide (56) and blade (46) as desired. In one example, active system actuator (336) keys movement of shiftable transducer assembly (354) to accommodate longitudinal movement of acoustic waveguide (56) and blade (46) for maintaining the predetermined alignment during articulation. Alternatively or in addition, active system actuator (336) directs movement of shiftable transducer assembly (354) to position blade (46) in any longitudinal position relative to shaft assembly (14) and/or clamp arm (44) as desired by the operator. In this respect, movement of shiftable transducer assembly (354) is independent upon articulation of articulation section (64) such that shiftable transducer assembly (354) may be moved with or without articulating articulation section (64). While articulation of articulation section (64) and/or shiftable transducer assembly (354) may be controlled by a robotic drive (not shown) as discussed in the present example, an operator may alternatively control articulation of articulation section (64) and/or shiftable transducer assembly (354) via a handle assembly (not shown), such as by a knob (not shown) operatively connected to articulation section (64) and/or shiftable transducer assembly (354). The invention is thus not intended to be unnecessarily limited to use with base assembly (312) as shown and described herein.

III. Exemplary Shift of Ultrasonic Blade with Shaft Assembly Articulation

Figures 12, 12A:
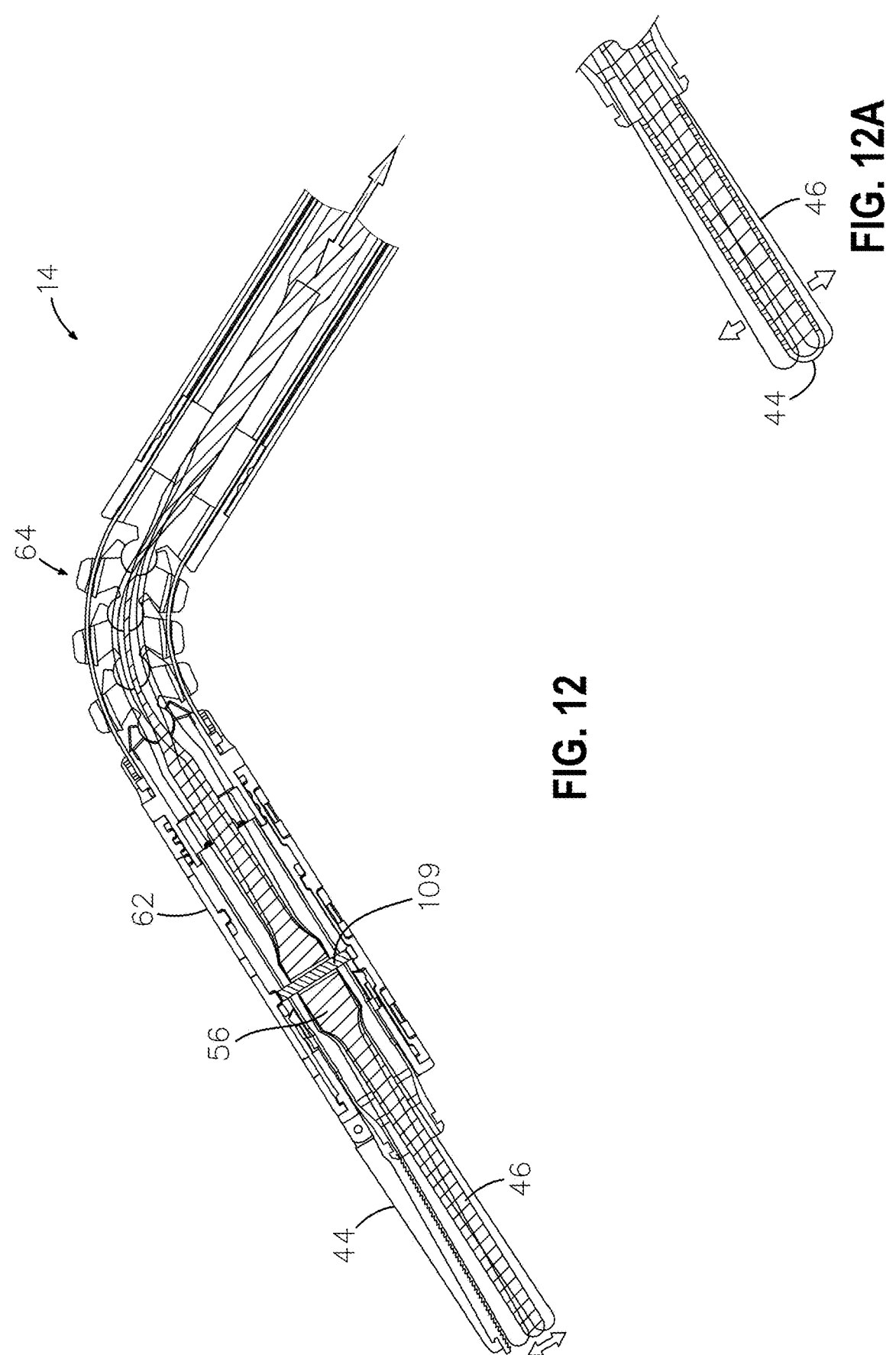
FIG. 12 depicts an enlarged, cross-sectional view of the ultrasonic surgical instrument of FIG. 1 taken along a centerline thereof showing a vertical movement of an ultrasonic blade of the end effector relative to a clamp arm of the end effector with the shaft assembly in the articulated configuration.
FIG. 12A depicts an enlarged, cross-sectional view of the ultrasonic surgical instrument of FIG. 1 taken along a centerline thereof showing a lateral movement of an ultrasonic blade of the end effector relative to a clamp arm of the end effector with the shaft assembly in the articulated configuration.

With respect to FIG. 12 and as described above, acoustic waveguide (56) may be pinned to distal shaft portion (62) using pin (109), which may also be referred to herein as distal waveguide pin (109). While distal waveguide pin (109) tends to aid in securing a longitudinal position of blade (46) relative to clamp arm (44) as noted above in relation to shifting of transducer assemblies (254, 354), forced bending of waveguide (56) via articulation of articulation section (64) results in a torque on waveguide (56) about distal waveguide pin (109). Unless the fit of distal waveguide pin (109) to waveguide (56) and distal shaft portion (62) is sufficiently rigid to resist such torque, this articulation creates a vertical misalignment between blade (46) and clamp arm (44), as shown in FIG. 12, even if distal waveguide pin (109) longitudinally holds blade (46) relative to clamp arm (44). For example, any articulation in an up or down motion as shown in FIG. 12 or in a left or right motion, as shown in FIG. 12A, may respectively result in vertical misalignment or lateral misalignment between blade (46) and clamp arm (44). Optionally, as shown in FIG. 12A, clamp arm (44) may be angularly positioned such that it rotates about an axis parallel to waveguide pin (109), such as rotating towards and away from a plane of articulation. Clamp arm (44) may also be angularly positioned such that it rotates within the plane of articulation, see clamp arm (44) of FIG. 12.

To this end, a compensator (400, 500, 600, 700), such as those discussed below, may be incorporated into instrument (10, 210, 310), to counter this torque by actively pushing or pulling on waveguide (56) while articulated to effectively correct the lateral or vertical misalignment between blade (46) and clamp arm (44). Moreover, such active pushing or pulling on waveguide (56) may be performed to generate any desired lateral or vertical alignment between blade (46) and clamp arm (44) such that the invention is not intended to be limited to only a planar alignment between blade (46) and clamp arm (44). In any case, like numbers below indicate like features described above in greater detail.

A. First Example Compensator

Figure 13A:
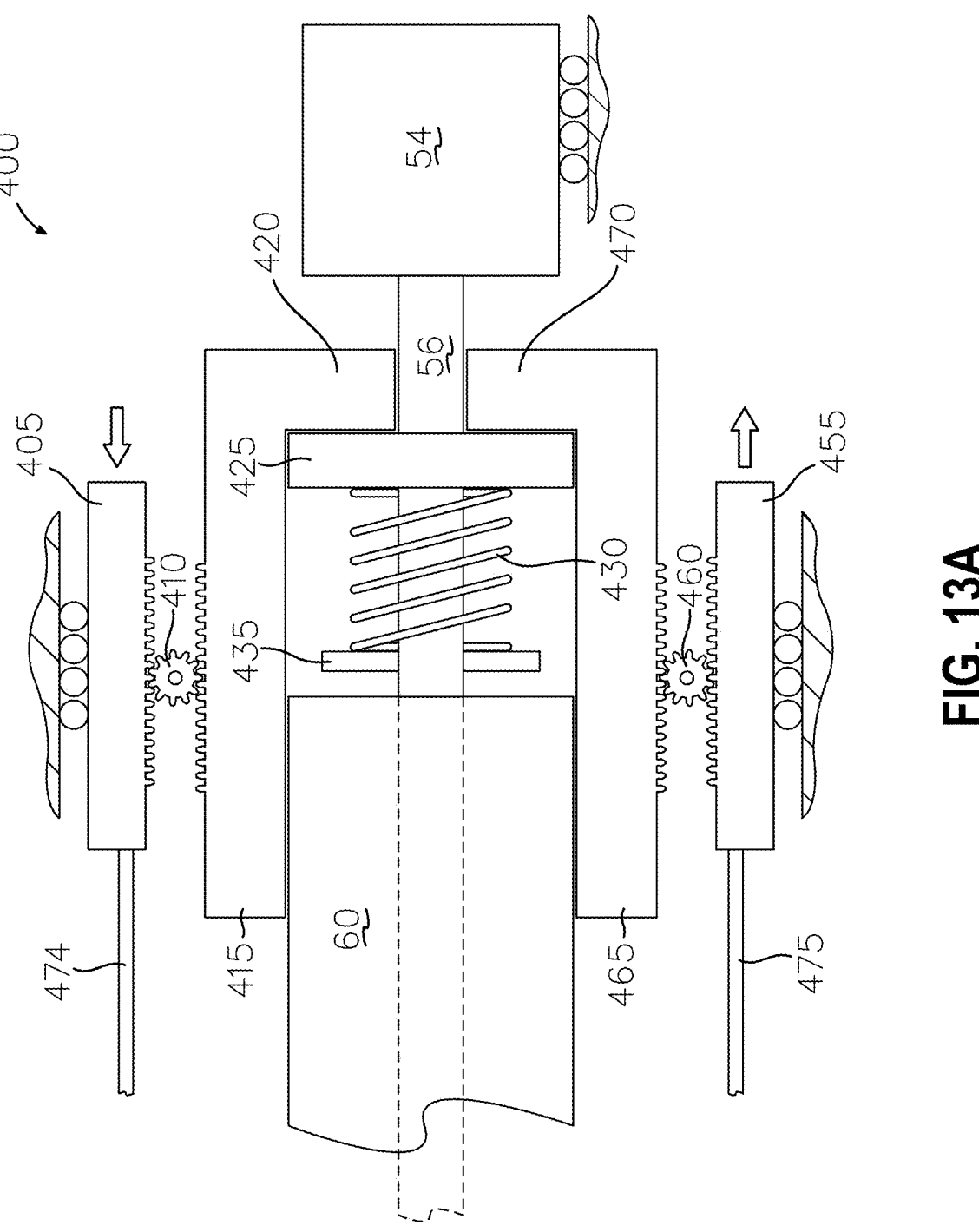
FIG. 13A depicts a schematic view of a first example of a compensator moving a first direction and being used to prevent a misalignment shown in FIG. 12 between the ultrasonic blade and the clamp arm.

FIG. 13A shows a first example of a compensator (400) used to adjust the above mentioned misalignment between blade (46) and clamp arm (44). In other words, as articulation section (64) articulates from the straight configuration to the articulated configuration, any misalignment between blade (46) and clamp arm (44) may be corrected through use of compensator (400).

Compensator (400) includes first and second band racks (405, 455), first and second pinion gears (410, 460), first and second blade racks (415, 465) with respective biasing arms (420, 470), a spring plunger (425), a blade bias spring (430), and a proximal waveguide pin (435). Band racks (405, 455) are each affixed to a respective articulation band (474, 475), which may be substantially similar to articulation bands (74) discussed above. Each band rack (405, 455) may be formed as a rack gear and be meshed with a respective pinion gear (410, 460). Each pinion gear (410, 460) is meshed with a respective blade rack (415, 465), which may also be formed as a rack gear. Each band rack (405, 455) and blade rack (415, 465) are positioned on opposing sides of a respective pinion gear (410, 460) such that as pinion gear (410, 460) rotates, band rack (405, 455) and blade rack (415, 465) translate in opposite directions to one another. In the present example, compensator (400) is positioned inside housing (700), although one or more portions of compensator (400) may be alternatively positioned within an instrument. Furthermore, while the present example includes pairs of band racks (405, 455), pinion gears (410, 460), and blade racks (415, 465), an alterative example may have one such band rack, pinion gear, and blade rack such that the invention is not intended to be unnecessarily limited to these pairs.

Each blade rack (415, 465) is integral or fixedly secured to a respective biasing arm (420, 470), which engages a spring plunger (425). In the present example, spring plunger (425) is situated to engage each biasing arm (420, 470) independently of the other. Spring plunger (425) is biased towards each of the biasing arms (420, 470) via a blade bias spring (430). Proximal waveguide pin (435), which is fixedly secured to a proximal portion of waveguide (56), is positioned on an opposite end of blade bias spring (430). With proximal waveguide pin (435) fixed to waveguide (56), any proximal or distal urging of proximal waveguide pin (435) similarly and collectively urges transducer assembly (54), waveguide (56), and blade (46) as parts of the acoustic drivetrain as discussed above. Therefore, transducer assembly (54) longitudinally slides as directed, such as via system actuator (236, 236) discussed above, whereas distal waveguide pin (109) shown in FIG. 12 secures the distal portion of waveguide (56) to distal shaft portion (62). Upon distally urging waveguide (56) of the acoustic drivetrain with compensator (400), waveguide (56) pivots about distal waveguide pin (109) to adjust alignment of blade (46). In the present example, distal waveguide pin (109) is secured or constrained to waveguide (56) with a predetermined fit configured to be sufficiently rigid so as to hold blade (46) relative to distal shaft portion (62) for ease of operator use while also being sufficiently loose to allow for waveguide (56) to pivot about distal waveguide pin (109). It will be appreciated that such predetermined fit may be tuned as desired such that the invention is not intended to be unnecessarily limited to the predetermined fit shown in the present example.

Figure 13B:
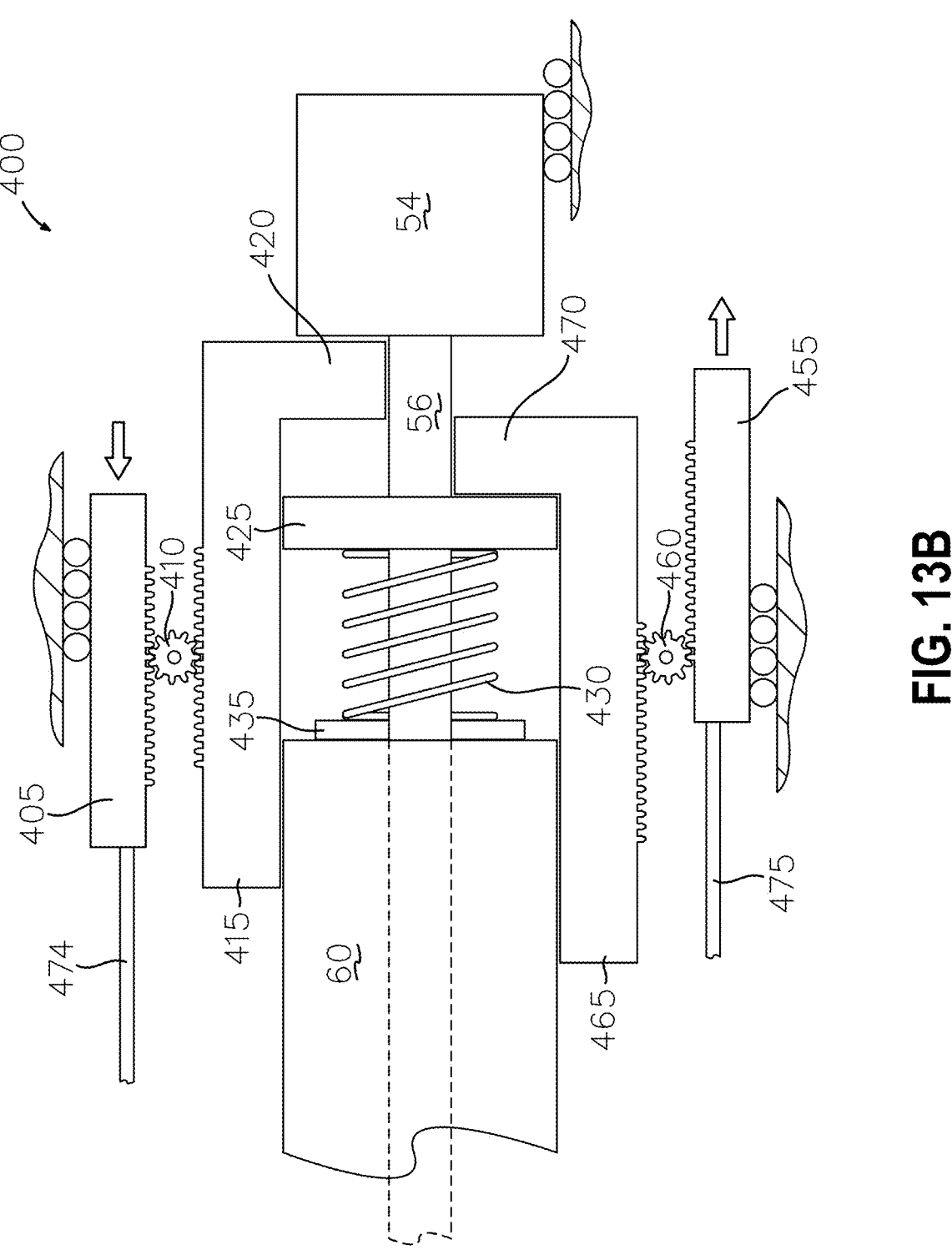
FIG. 13B depicts a schematic view of the first example of the compensator of FIG. 13A moving in a second direction.

As an example of operation as shown in relation to FIG. 12 and FIGS. 13A-13B, a distally directed articulation input force shown in FIG. 13A distally translates first band rack (405) and thus drives a counter-clockwise rotation of first pinion gear (410). In turn, counter-clockwise rotation of first pinion gear (410) thereby translates first blade rack (415) in a proximal direction, thereby forming a gap between first biasing arm (420) and spring plunger (425). On the lower side, a proximally directed articulation input force proximally translates second band rack (455) and thus drives a counter-clockwise rotation of second pinion gear (460). In turn, counter-clockwise rotation of pinion gear (460) thereby translates second blade rack (465) in a distal direction to thus apply a distally directed force on spring plunger (425). Applying such distally directed force on spring plunger (425) compresses plunger spring (430) to thereby apply a distally directed force on proximal waveguide pin (435) urging the acoustic drivetrain, including transducer assembly (54), waveguide (56), and blade (46), in a distal direction and, in turn, pivot blade (46) about distal waveguide pin (109) into a desired alignment as discussed above. In one example, during translation of blade (46) and transducer (54), plunger spring (430) may compress to absorb an initial force impulse to inhibit any impact on blade (46) from affecting biasing arm (470) during use.

While the present example in FIGS. 13A-13B depict second biasing arm (470) translated in the distal direction to distally translate waveguide (56) for adjusting alignment of blade (46), first biasing arm (420) may act in a like manner should the forces and directions applied to band racks (405, 455) be reversed as discussed above. In other words, the top portion of compensator (400) including first band rack (405) operates in a like manner as the bottom portion including second band rack (455).

As shown in the present example, first band rack (405), first pinion gear (410), and first blade rack (415) are collectively configured to be driven with predetermined gear ratios for adjusting blade (46) based on translation of first band rack (405). In this respect, a predetermined amount of articulation of articulation section (64) results in a predetermined amount of blade (46) adjustment. In this respect, second band rack (455), second pinion gear (460), and second blade rack are similarly configured to be driven with predetermined gear ratios upon articulation section (64) in the opposite direction. The predetermined alignment in one example positions blade (46) to be directly opposite of clamp arm (44) throughout articulation, such as aligning in a common plane. Alternative predetermined alignments may be similarly configured such that the invention is not intended to be unnecessarily limited to such direct alignment between blade (46) and clamp arm (44). Still, with opposing forces being applied to band racks (405, 455), backlash between the forces applied and rack gears (415, 465) may occur in some instances while articulation and alignment of blade (46) with one input body, such as one of pucks (38a, 38b, 38c, 38d, 38e, 38f). In other words, directly driving band racks (405, 455) may result in a larger amount of play at rack gears (415, 465). Therefore, in other examples, compensators, such as compensators (500, 600, 700), may be alternatively driven to reduce backlash in some instances, such that the invention is not intended to be unnecessarily limited to compensator (400) discussed above.

B. Second Example Compensator

Figure 14A:
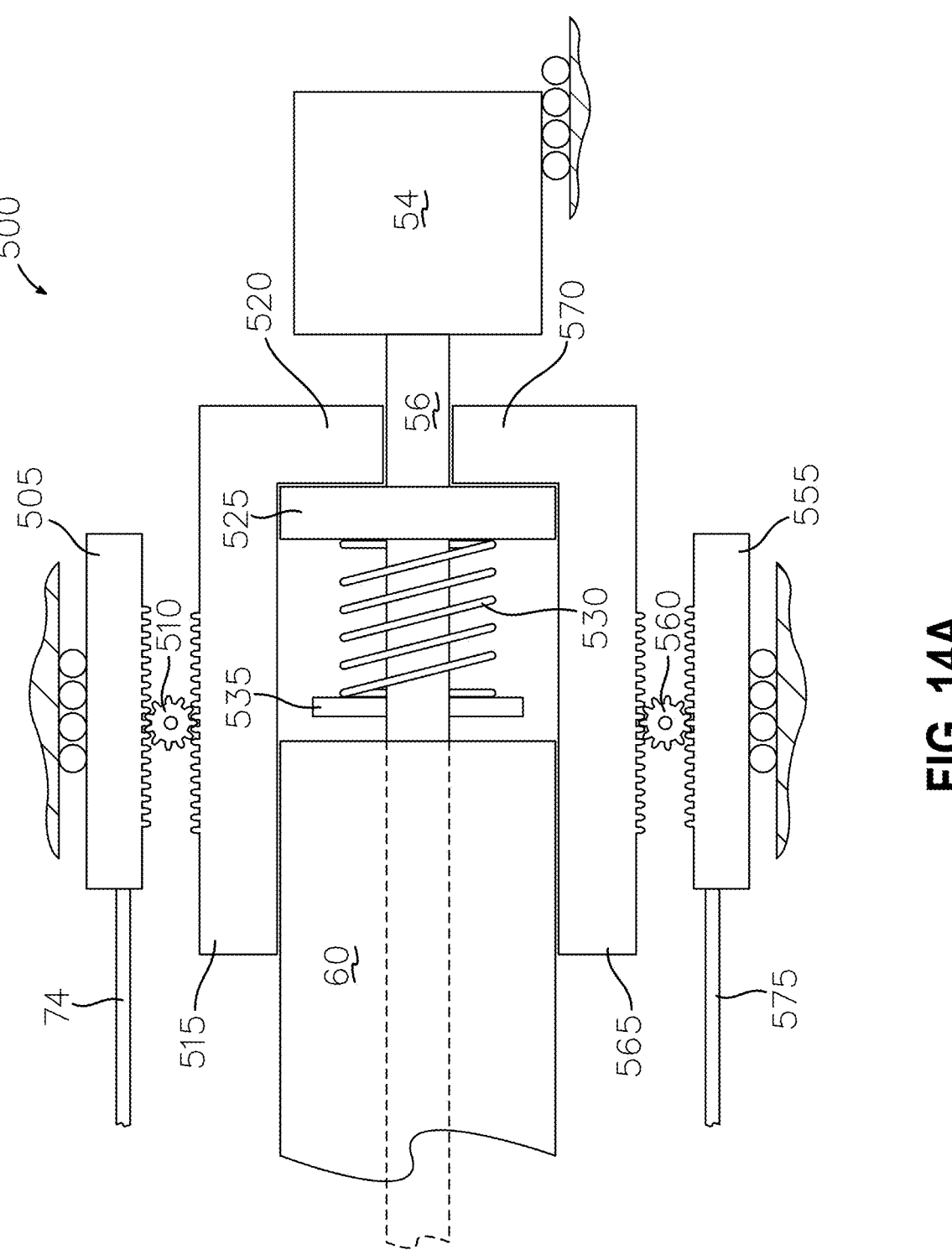
FIG. 14A depicts a schematic view of a second example of a compensator moving a first direction and being used to prevent the misalignment shown in FIG. 12 between the ultrasonic blade and the clamp arm.
Figure 14B:
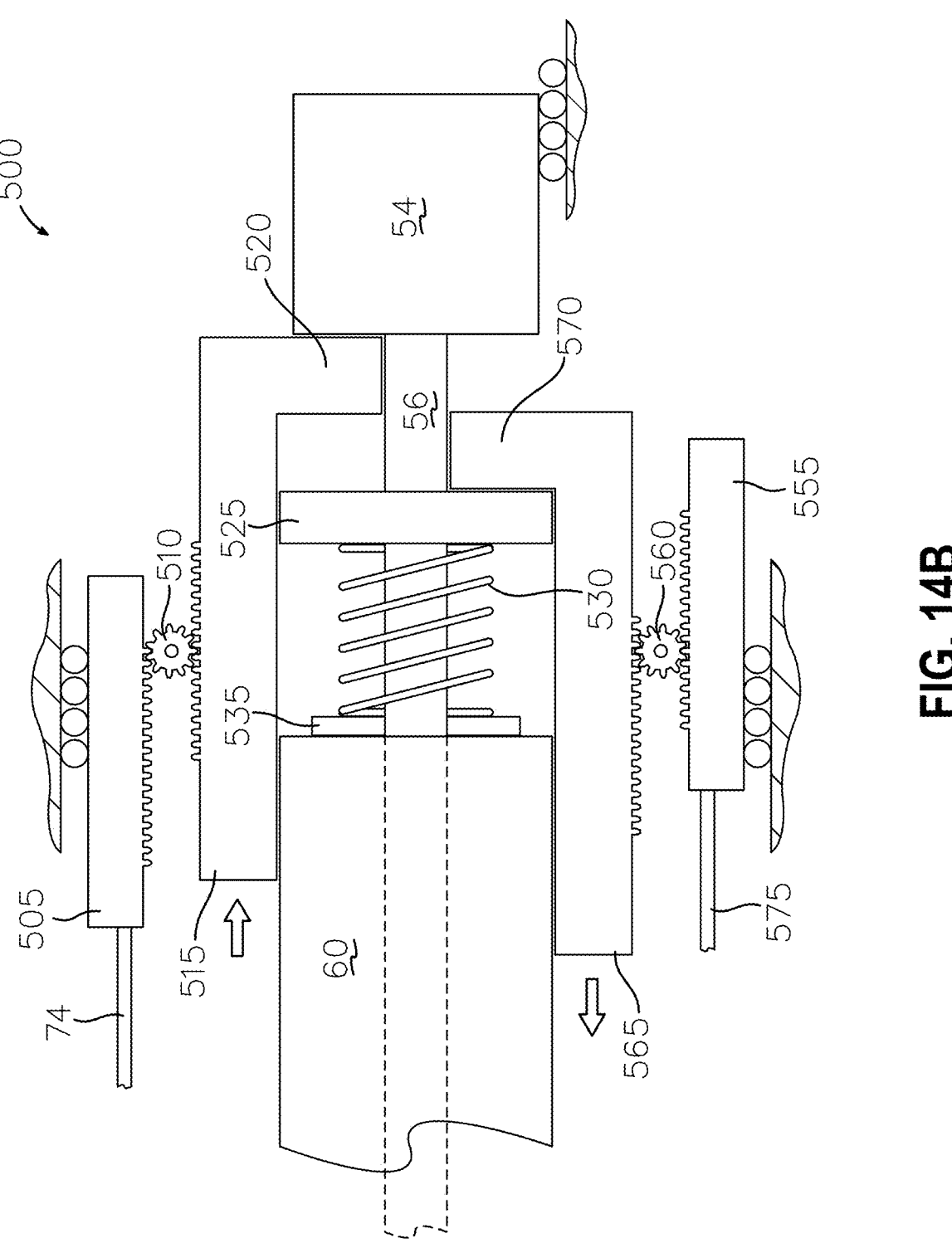
FIG. 14B depicts a schematic view of the second example of the compensator of FIG. 14A moving in a second direction.

FIG. 14A shows compensator (500) which is substantially similar to compensator (400) unless otherwise discussed below, but with the articulation input force being applied to blade racks (515, 565) to thereby drive movement of the articulation bands (574, 575) and spring plunger (525). Articulation of articulation section (64) and alignment of blade (46) therefore are still being driven by one input body, such as one of pucks (38a, 38b, 38c, 38d, 38e, 38f), in the present example. FIG. 14B shows compensator (500) but with the articulation input forces having been applied such that the backlash is greatest at band racks (505, 555).

C. Third Example Compensator

Figure 15A:
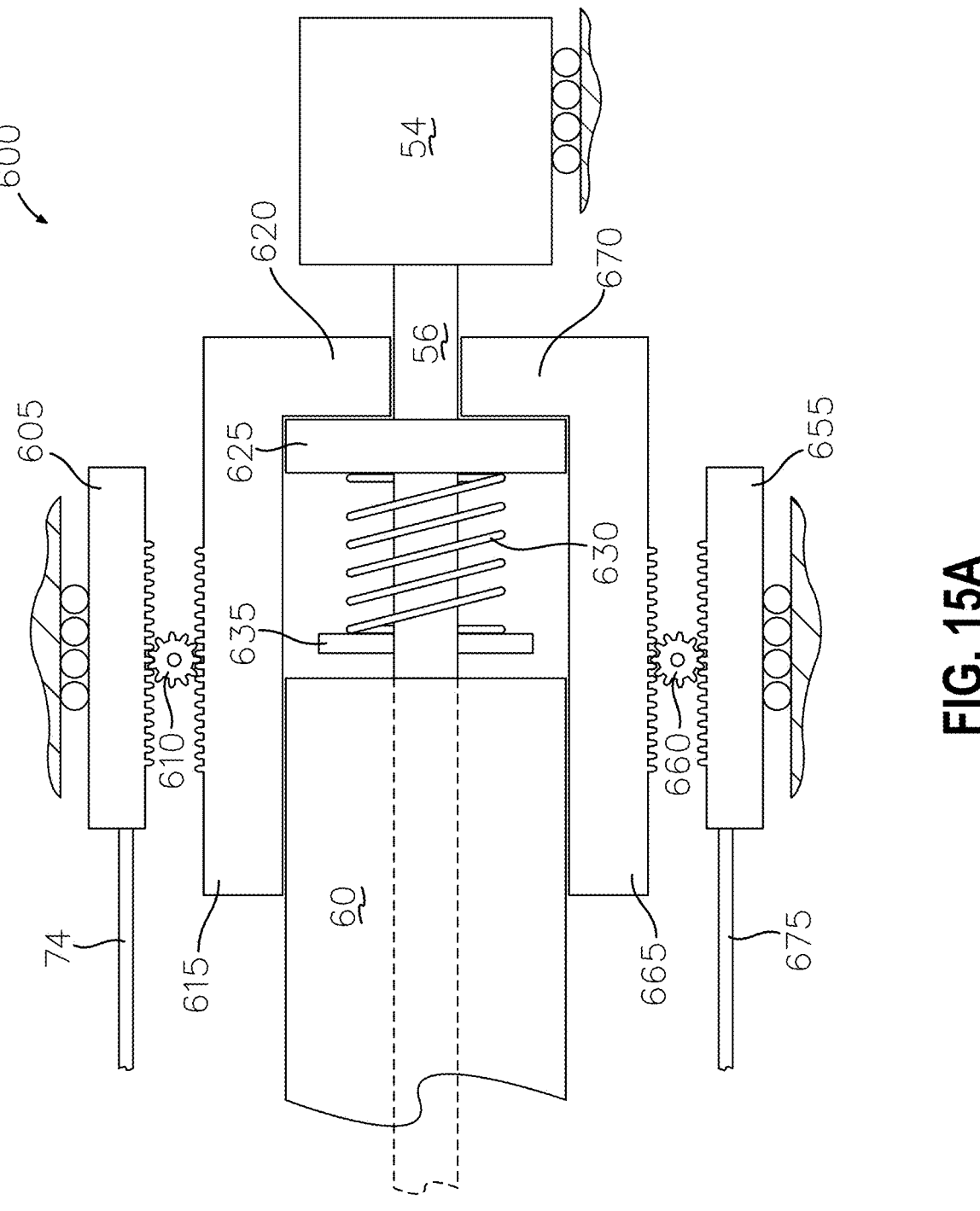
FIG. 15A depicts a schematic view of a third example of a compensator moving a first direction and being used to prevent the misalignment shown in FIG. 12 between the ultrasonic blade and the clamp arm.
Figure 15B:
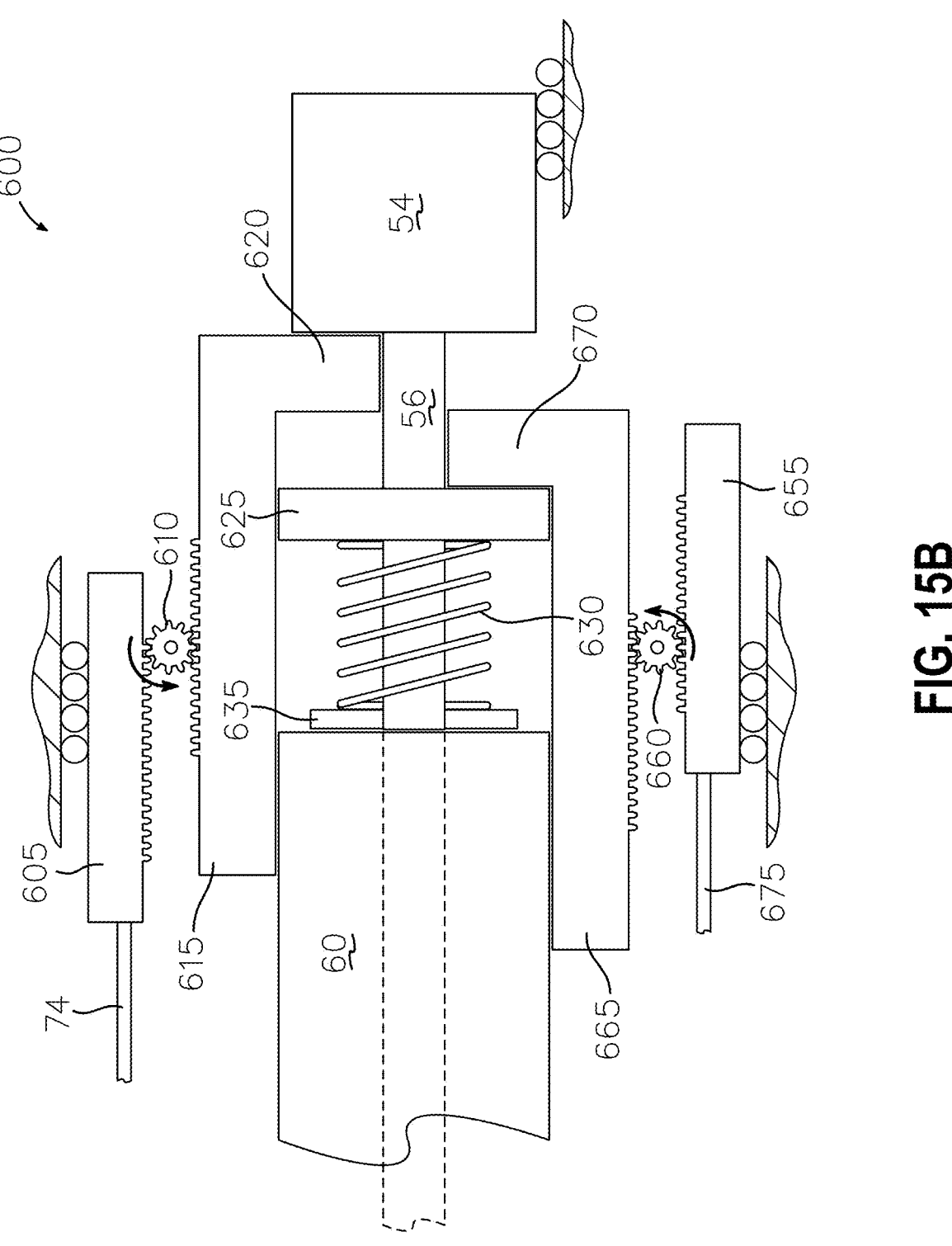
FIG. 15B depicts a schematic view of the third example of the compensator of FIG. 15A moving in a second direction.

FIG. 15A shows compensator (600) which is substantially similar to compensators (400, 500) unless otherwise discussed below, but with an articulation input torque being applied to pinion gears (610, 660) to thereby drive movement of the articulation bands (674, 675) and spring plunger (625). Articulation of articulation section (64) and alignment of blade (46) therefore are still being driven by one input body, such as one of pucks (38a, 38b, 38c, 38d, 38e, 38f), in the present example. FIG. 15B shows compensator (600) but with the articulation input forces having been applied such that the backlash is equal between band racks (605, 655) and respective blade racks (615, 665).

D. Fourth Example Compensator

Figure 16:
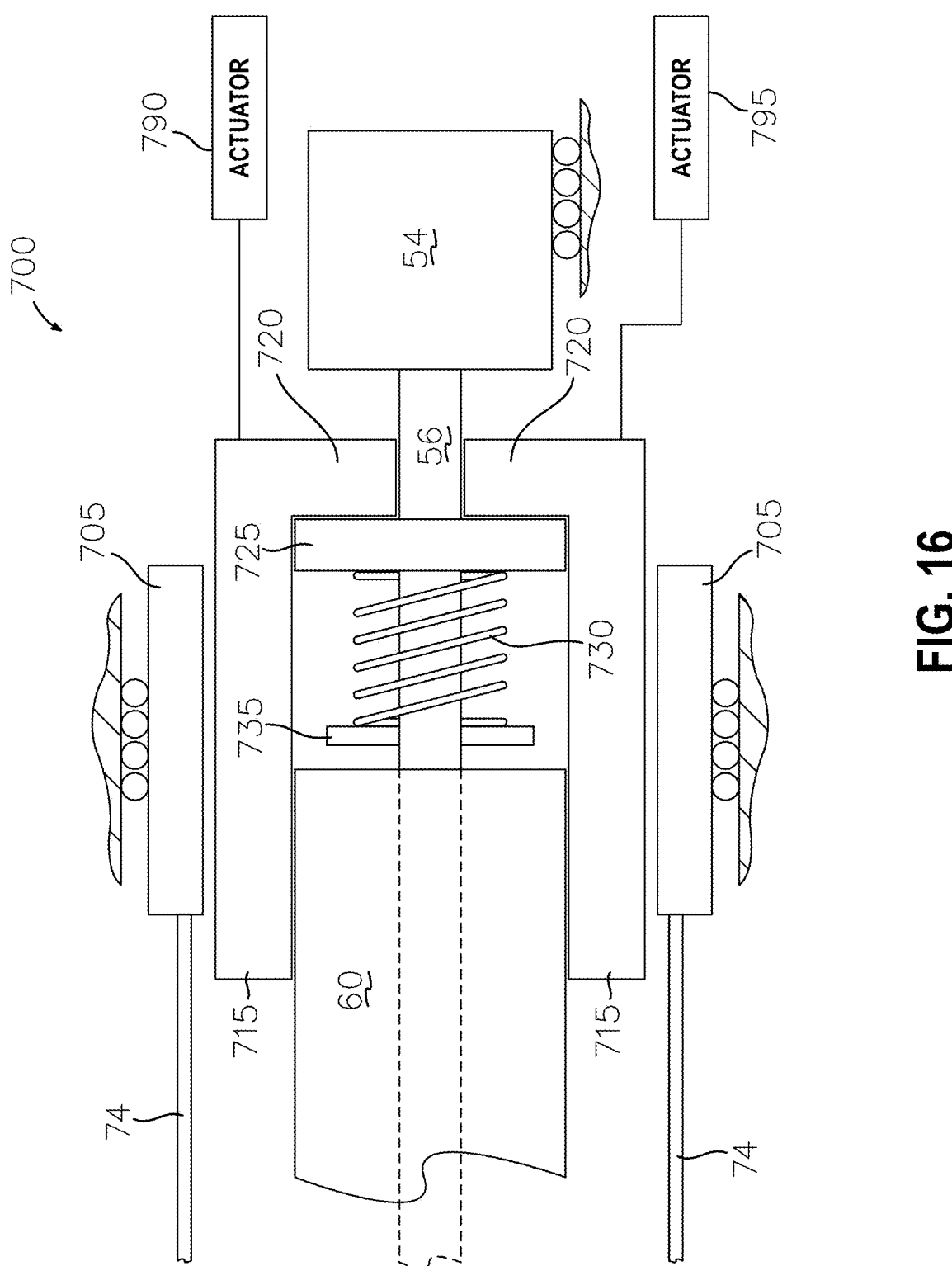
FIG. 16 depicts a schematic view of a fourth example of a compensator being used to prevent the misalignment shown in FIG. 12 between the ultrasonic blade and the clamp arm.

FIG. 16 shows compensator (700) having actuators (790, 795) being directly linked to blade racks (615, 665) to thereby drive translation of biasing arms (720, 770). On an occasion where each of the input bodies, such as pucks (38*a*, 38*b*, 38*c*, 38*d*, 38*e*, 38*f*), have been accounted for performing a function other than compensating, it may be advantageous to compensate using software. Compensator (700) is capable of compensating using software and without require the use of an input body (38*a*, 38*b*, 38*c*, 38*d*, 38*e*, 38*f*). A sensor or processor may be positioned anywhere within ultrasonic surgical instrument (10) to directly or indirectly determine if a misalignment between blade (46) and clamp arm (44) exists. If such a misalignment does exist, compensator (700) may be capable of aligning blade (46) and clamp arm (44) by driving blade racks (715, 765) as described above.

IV. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: an end effector including an ultrasonic blade; a shaft assembly proximally extending from the end effector and defining a longitudinal axis, wherein the shaft assembly includes: an articulation section configured to articulate from a straight configuration to an articulated configuration to thereby deflect the end effector relative to the longitudinal axis, an acoustic waveguide having a flexible waveguide portion positioned within the articulation section, a distal waveguide portion acoustically connected to the ultrasonic blade, and a proximal waveguide portion positioned proximal to the articulation section, an articulation band configured to drive the articulation of the articulation section between the straight configuration and the articulated configuration, and a pin distal to the articulation section and configured to constrain the distal waveguide portion to the end effector; and a body assembly proximally extending from the shaft assembly, including: a housing, a transducer assembly secured to the acoustic waveguide and configured to translate the acoustic waveguide along the shaft assembly, and a compensator operatively connected to the articulation band and the acoustic waveguide, the compensator configured to longitudinally urge the acoustic waveguide along the longitudinal axis to thereby pivot the ultrasonic blade about the pin for alignment relative to another portion of the end effector.

Example 2

The ultrasonic surgical instrument of Example 1, wherein the articulation band including a band rack gear secured to a proximal end of the articulation band, the compensator including: a blade rack gear secured to the proximal waveguide portion, and an articulation pinion gear meshed between the band rack gear and the blade rack gear.

Example 3

The ultrasonic surgical instrument of Example 2, wherein the compensator is further configured to apply an opposing translation to the articulation band relative to the acoustic waveguide.

Example 4

The ultrasonic surgical instrument of any one or more of Examples 2 through 3, wherein the articulation pinion gear is housed inside of the housing.

Example 5

The ultrasonic surgical instrument of any one or more of Examples 2 through 4, wherein the pin including a distal blade pin, the compensator further including a proximal blade pin, a blade bias spring, and a spring plunger, the proximal blade pin secured to the proximal waveguide portion, the blade bias spring configured to apply a force to each of the spring plunger and the proximal blade pin.

Example 6

The ultrasonic surgical instrument of Example 5, the spring plunger configured to apply pressure on the blade rack gear.

Example 7

The ultrasonic surgical instrument of any one or more of Examples 2 through 6, wherein the body assembly further includes an articulation driver configured to apply an articulation force to thereby drive articulation.

Example 8

The ultrasonic surgical instrument of Example 7, wherein the articulation force is configured to be applied to the blade rack gear.

Example 9

The ultrasonic surgical instrument of Example 7, wherein the the articulation force is configured to be applied to the articulation pinion gear.

Example 10

The ultrasonic surgical instrument of Example 7, wherein the articulation force is configured to be applied to the band rack gear.

Example 11

The ultrasonic surgical instrument of any one or more of Examples 1 through 10, the end effector further including a clamp arm extending along an arm axis and configured to clamp tissue between the clamp arm and the ultrasonic blade, the blade extending along a blade axis, the compensator configured to align the arm axis and the blade axis so as to be positioned in a common plane.

Example 12

The ultrasonic surgical instrument of any one or more of Examples 1 through 11, wherein the compensator is operatively linked to the articulation band and the acoustic waveguide.

Example 13

The ultrasonic surgical instrument of any one or more of Examples 1 through 12, the articulation band including a first articulation band, the shaft assembly further including a second articulation band, the first articulation band including a first band rack gear secured to a proximal end of the first articulation band, the second articulation band including a second band rack gear secured to a proximal end of the second articulation band, the compensator including: a first blade rack gear and a second blade rack gear, wherein each of the first and second blade rack gears is secured to the proximal waveguide portion, a first articulation pinion gear meshed between the first band rack gear and the first blade rack gear, and a second articulation pinion gear meshed between the second band rack gear and the second blade rack gear.

Example 14

The ultrasonic surgical instrument of Example 13, wherein the first and second articulation bands are configured to translate independent of one another.

Example 15

The ultrasonic surgical instrument of any one or more of Examples 1 through 14, the end effector further including a clamp arm configured to clamp tissue between the clamp arm and the ultrasonic blade, the compensator configured to maintain relative positioning between the clamp arm and the ultrasonic blade during articulation from the straight configuration to the articulated configuration.

Example 16

An ultrasonic surgical instrument, comprising: an end effector, including: clamp arm configured to selectively move from an open position toward a closed position, and an ultrasonic blade longitudinally fixed relative to the clamp arm in a predetermined longitudinal position, a shaft assembly proximally extending from the end effector, wherein the shaft assembly includes: a proximal shaft portion defining a longitudinal axis, a distal shaft portion supporting the end effector and distally extending therefrom, an articulation section positioned between the proximal and distal shaft portions, wherein the articulation section is configured to articulate from a straight configuration to an articulated configuration to thereby deflect the end effector relative to the longitudinal axis, an acoustic waveguide having a distal waveguide portion, a proximal waveguide portion and a flexible waveguide portion positioned therebetween within the articulation section, wherein the distal waveguide portion is acoustically connected to the ultrasonic blade; and a body assembly proximally extending from the shaft assembly, including: a transducer assembly secured to the proximal waveguide portion on the longitudinal axis and configured to generate an ultrasonic energy, a compensator configured to maintain a relative positioning between the clamp arm and the ultrasonic blade during articulation of the articulation section from the straight configuration to the articulated configuration.

Example 17

The ultrasonic surgical instrument of Example 16, the shaft assembly further including an articulation band configured to drive the articulation of the articulation section between the straight configuration and the articulated configuration, the articulation band in operable communication with the compensator.

Example 18

The ultrasonic surgical instrument of Example 17, the articulation band including a band rack gear secured to a proximal end of the articulation band, the compensator including: a blade rack gear secured to the proximal waveguide portion, and an articulation pinion gear meshed between the band rack gear and the blade rack gear.

Example 19

The ultrasonic surgical instrument of any one or more of Examples 16 through 18, the shaft assembly further including a pin distal to the articulation section and configured to constrain the distal waveguide portion to the end effector.

Example 20

A method of aligning an ultrasonic blade with a clamp arm of an ultrasonic surgical instrument, comprising: articulating an articulation section of the ultrasonic surgical instrument from a straight configuration to an articulated configuration; and during the articulation, maintaining a relative alignment between the clamp arm and the ultrasonic blade.

V. Miscellaneous

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873, 873; 5,980,510; 6,325,811; 6,773,444; 6,783,524; 9,095, 367; U.S. Pub. No. 2006/0079874; U.S. Pub. No. 2007/ 0191713; U.S. Pub. No. 2007/0282333; U.S. Pub. No. 2008/0200940; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265; U.S. Pat. No. 9,393,037, issued Jul. 19, 2016; U.S. Pat. No. 10,172, 636, issued Jan. 8, 2019; and/or U.S. Pat. App. No. 61/410, 603. The disclosures of each of the foregoing patents, publications, and applications are incorporated by reference herein. It should also be understood that the instruments described herein may have various structural and functional similarities with the HARMONIC ACER Ultrasonic Shears, the HARMONIC WAVER Ultrasonic Shears, the HAR- MONIC FOCUS® Ultrasonic Shears, and/or the HAR-MONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HAR-MONIC ACER Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HAR-MONIC ACER Ultrasonic Shears, the HARMONIC WAVER Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into another example of a robotic surgical system, and those of ordinary skill in the art will recognize that various teachings herein may be readily combined with various teachings of any of the following: U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No.

8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An ultrasonic surgical instrument, comprising:
(a) an end effector including an ultrasonic blade;
(b) a shaft assembly proximally extending from the end effector and defining a longitudinal axis, wherein the shaft assembly includes:
(i) an articulation section configured to articulate from a straight configuration to an articulated configuration to thereby deflect the end effector relative to the longitudinal axis,
(ii) an acoustic waveguide having a flexible waveguide portion positioned within the articulation section, a distal waveguide portion acoustically connected to the ultrasonic blade, and a proximal waveguide portion positioned proximal to the articulation section, (iii) an articulation band including a band rack gear secured to a proximal end of the articulation band and configured to drive the articulation of the articulation section between the straight configuration and the articulated configuration, and (iv) a pin distal to the articulation section and configured to constrain the distal waveguide portion to the end effector; and (c) a body assembly proximally extending from the shaft assembly, including:

(i) a housing, (ii) a transducer assembly secured to the acoustic waveguide and configured to translate the acoustic waveguide along the shaft assembly, and (iii) a compensator operatively connected to the articulation band and the acoustic waveguide, the compensator configured to longitudinally urge the acoustic waveguide along the longitudinal axis to thereby pivot the ultrasonic blade about the pin for alignment relative to another portion of the end effector, wherein the compensator includes:

(A) a blade rack gear secured to the proximal waveguide portion, and (B) an articulation pinion gear meshed between the band rack gear and the blade rack gear.

2. The ultrasonic surgical instrument of claim 1, wherein the compensator is further configured to apply an opposing translation to the articulation band relative to the acoustic waveguide.

3. The ultrasonic surgical instrument of claim 1, wherein the articulation pinion gear is housed inside of the housing.

4. The ultrasonic surgical instrument of claim 1, wherein the pin including a distal blade pin, the compensator further including a proximal blade pin, a blade bias spring, and a spring plunger, the proximal blade pin secured to the proximal waveguide portion, the blade bias spring configured to apply a force to each of the spring plunger and the proximal blade pin.

5. The ultrasonic surgical instrument of claim 4, where the spring plunger is configured to apply pressure on the blade rack gear.

6. The ultrasonic surgical instrument of claim 1, wherein the body assembly further includes an articulation driver configured to apply an articulation force to thereby drive articulation.

7. The ultrasonic surgical instrument of claim 6, wherein the articulation force is configured to be applied to the blade rack gear.

8. The ultrasonic surgical instrument of claim 6, wherein the articulation force is configured to be applied to the articulation pinion gear.

9. The ultrasonic surgical instrument of claim 6, wherein the articulation force is configured to be applied to the band rack gear.

10. The ultrasonic surgical instrument of claim 1, the end effector further including a clamp arm extending along an arm axis and configured to clamp tissue between the clamp arm and the ultrasonic blade, the blade extending along a blade axis, the compensator configured to align the arm axis and the blade axis so as to be positioned in a common plane.

11. The ultrasonic surgical instrument of claim 1, the articulation band including a first articulation band, the shaft assembly further including a second articulation band, the band rack gear being a first band rack gear, the blade rack gear being a first blade rack gear, the articulation pinion being a first articulation pinion, the second articulation band including a second band rack gear secured to a proximal end of the second articulation band, the compensator further including:

(A) a second blade rack gear, wherein each of the first and second blade rack gears is secured to the proximal waveguide portion, and (B) a second articulation pinion gear meshed between the second band rack gear and the second blade rack gear.

12. The ultrasonic surgical instrument of claim 11, wherein the first and second articulation bands are configured to translate independent of one another.

13. The ultrasonic surgical instrument of claim 1, the end effector further including a clamp arm configured to clamp tissue between the clamp arm and the ultrasonic blade, the compensator configured to maintain relative positioning between the clamp arm and the ultrasonic blade during articulation from the straight configuration to the articulated configuration.

14. An ultrasonic surgical instrument, comprising:

(a) an end effector, including:

(i) a clamp arm configured to selectively move from an open position toward a closed position, and (ii) an ultrasonic blade longitudinally fixed relative to the clamp arm in a predetermined longitudinal position, (b) a shaft assembly proximally extending from the end effector, wherein the shaft assembly includes:

(i) a proximal shaft portion defining a longitudinal axis, (ii) a distal shaft portion supporting the end effector and distally extending therefrom, (iii) an articulation section positioned between the proximal and distal shaft portions, wherein the articulation section is configured to articulate from a straight configuration to an articulated configuration to thereby deflect the end effector relative to the longitudinal axis, (iv) an acoustic waveguide having a distal waveguide portion, a proximal waveguide portion and a flexible waveguide portion positioned therebetween within the articulation section, wherein the distal waveguide portion is acoustically connected to the ultrasonic blade, and (v) an articulation band including a band rack gear secured to a proximal end of the articulation band and configured to drive the articulation of the articulation section between the straight configuration and the articulated configuration; and (c) a body assembly proximally extending from the shaft assembly, including:

(i) a transducer assembly secured to the proximal waveguide portion on the longitudinal axis and configured to generate an ultrasonic energy, (ii) a compensator configured to maintain a relative positioning between the clamp arm and the ultrasonic blade during articulation of the articulation section from the straight configuration to the articulated configuration, wherein the compensator includes:

(A) a blade rack gear secured to the proximal waveguide portion, and (B) an articulation pinion gear meshed between the band rack gear and the blade rack gear.

15. The ultrasonic surgical instrument of claim 14, the shaft assembly further including a pin distal to the articulation section and configured to constrain the distal waveguide portion to the end effector.

16. An ultrasonic surgical instrument, comprising:

(a) an end effector including an ultrasonic blade;

(b) a shaft assembly proximally extending from the end effector and defining (b) a longitudinal axis, wherein the shaft assembly includes:

(i) an articulation section configured to articulate from a straight configuration to an articulated configuration to thereby deflect the end effector relative to the longitudinal axis, (ii) an acoustic waveguide having a flexible waveguide portion positioned within the articulation section, a distal waveguide portion acoustically connected to the ultrasonic blade, and a proximal waveguide portion positioned proximal to the articulation section, (iii) an articulation band configured to drive the articulation of the articulation section between the straight configuration and the articulated configuration, and (iv) a distal blade pin distal to the articulation section and configured to constrain the distal waveguide portion to the end effector; and (c) a body assembly proximally extending from the shaft assembly, including:

(i) a housing, (ii) a transducer assembly secured to the acoustic waveguide and configured to translate the acoustic waveguide along the shaft assembly, (iii) a compensator operatively connected to the articulation band and the acoustic waveguide, the compensator configured to longitudinally urge the acoustic waveguide along the longitudinal axis to thereby pivot the ultrasonic blade about the distal blade pin for alignment relative to another portion of the end effector, (iv) a proximal blade pin, secured to the proximal waveguide portion (v) a blade bias member, and (vi) a biased plunger, wherein the blade bias member is configured to apply a force to each of the biased plunger and the proximal blade pin.

17. The ultrasonic surgical instrument of claim 16, wherein blade bias member is a blade bias spring.

18. The ultrasonic surgical instrument of claim 16, wherein the biased plunger is a spring plunger.

19. The ultrasonic surgical instrument of claim 16, wherein blade bias member is a blade bias spring, and wherein the biased plunger is a spring plunger.

20. The ultrasonic surgical instrument of claim 16, where the spring biased plunger is configured to apply pressure on the blade rack gear.

* * * * *